(12) United States Patent
Baker et al.

(10) Patent No.: US 11,424,031 B2
(45) Date of Patent: Aug. 23, 2022

(54) DIGITAL BIOMARKERS FOR PROGRESSING MS

(71) Applicant: Hoffmann-La Roche Inc., Little Falls, NJ (US)

(72) Inventors: Mike Baker, Basel (CH); Shibeshih Mitiku Belachew, Basel (CH); Christian Gossens, Basel (CH); Michael Lindemann, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 142 days.

(21) Appl. No.: 16/351,091

(22) Filed: Mar. 12, 2019

(65) Prior Publication Data

US 2019/0214140 A1    Jul. 11, 2019

Related U.S. Application Data

(63) Continuation of application No. PCT/EP2017/073137, filed on Sep. 14, 2017.

(30) Foreign Application Priority Data

Sep. 14, 2016  (EP) .................................. 16188849

(51) Int. Cl.
   *G16H 50/20*    (2018.01)
   *G16H 10/20*    (2018.01)
(52) U.S. Cl.
   CPC ............. *G16H 50/20* (2018.01); *G16H 10/20* (2018.01)
(58) Field of Classification Search
   CPC ........ G16H 10/00; G16H 10/40; G16H 15/00; G16H 20/00; G16H 20/10; G16H 20/13;
   (Continued)

(56) References Cited

U.S. PATENT DOCUMENTS

2003/0013981 A1 *  1/2003  Gevins ................... A61B 5/377
                                                        600/544
2008/0183395 A1 *  7/2008  Bevilacqua ............ C12Q 1/689
                                                         702/19
(Continued)

FOREIGN PATENT DOCUMENTS

JP     2014-510557 A    5/2014
JP     2015-500042 A    1/2015
(Continued)

OTHER PUBLICATIONS

Oung, Qi Wei et al. "Technologies for Assessment of Motor Disorders in Parkinson's Disease: A Review." Sensors (Basel, Switzerland) vol. 15,9 21710-45. Aug. 31, 2015, doi:10.3390/s150921710.*

(Continued)

*Primary Examiner* — Robert W Morgan
*Assistant Examiner* — Charles P Coleman
(74) *Attorney, Agent, or Firm* — Bose McKinney & Evans LLP

(57) ABSTRACT

The present disclosure relates to the field of diagnostics, specifically, to a method of identifying progressing multiple sclerosis (MS) in a subject. At least one performance parameter is determined from a dataset of activity measurements obtained from the subject using a mobile device, and the performance parameter is compared to a reference, whereby a subject with progressing MS will be identified. Also disclosed is a method of recommending an anti-CD20 antibody therapy against MS that includes the steps just mentioned and the further step of recommending the anti-CD20 antibody therapy if the subject suffers from progressing MS. Also disclosed is a mobile device having a processor, at least one sensor and a database as well as software which is tangibly embedded to the device and, when running on said device, carries out the method of this disclosure as (Continued)

well as the use of such a device for identifying a subject suffering from progressing MS.

20 Claims, 17 Drawing Sheets

(58) Field of Classification Search
CPC ........ G16H 20/17; G16H 30/00; G16H 40/00; G16H 50/00; G16H 70/00; G16H 80/00; G16H 50/20; G16H 10/20
USPC .................................................. 705/2, 3, 20
See application file for complete search history.

(56) References Cited

U.S. PATENT DOCUMENTS

| | | | |
|---|---|---|---|
| 2013/0203475 A1* | 8/2013 | Kil .......................... | A63F 13/21 463/7 |
| 2014/0153794 A1* | 6/2014 | Varaklis ................ | G06T 7/0012 382/128 |
| 2015/0005674 A1* | 1/2015 | Schindler ............. | A61B 5/1121 600/595 |
| 2015/0110741 A1* | 4/2015 | Cadavid ................. | A61B 5/168 424/85.6 |
| 2015/0179079 A1* | 6/2015 | Rodriguez, Jr. ..... | A61B 5/1124 434/236 |
| 2015/0220693 A1* | 8/2015 | Cadavid ................. | G16H 50/30 424/133.1 |
| 2016/0054320 A1* | 2/2016 | Schubert .............. | A61K 38/215 424/78.37 |
| 2016/0066820 A1 | 3/2016 | Sales et al. | |
| 2017/0258390 A1* | 9/2017 | Howard ................... | A61B 5/16 |
| 2018/0001184 A1* | 1/2018 | Tran ........................ | G06F 1/163 |

FOREIGN PATENT DOCUMENTS

WO  WO 2012/101093 A2  8/2012
WO  WO 2015/118534 A1  8/2015

OTHER PUBLICATIONS

Ortiz-Gutiérrez, Rosa et al. "A telerehabilitation program improves postural control in multiple sclerosis patients: a Spanish preliminary study." International journal of environmental research and public health vol. 10,11 5697-710. Oct. 31, 2013, doi: 10.3390/ijerph10115697.*
Tacchino et al., "Anew app for at-home cognitive training," JMIR Mhealth Uhealth, Jul.-Sep. 2015, 3(3):e85.*
Stark et al., "The quantified brain: a framework for mobile device-based assessment of behavior and neurological function," Applied Clinical Informatics, 2017: 7:290-298.*
Stuart et al., "A protocol to examine vision and gat in Parkinson's disease: impact of cognition and response to visual cues," F1000Research 2016, 4:1379.*
Zhai et al., "Smartphone accelerometry: a smart and reliable measurement of real-life physical activity in multiple sclerosis and healthy individuals," Frontier in Neuroloty, Aug. 2020, vol. 11, Article 688.*
Aktas et al., Neuronal Damage in Autoimmune Neuroinflammation Mediated by the Death Ligand TRAIL, Neuron, May 5, 2005, pp. 421-432, vol. 46.
Zamvil et al., Diverse Targets for Intervention During Inflammatory and Neurodegenerative Phases of Multiple Sclerosis, Neuron, Jun, 5, 2003, pp. 685-688, vol. 38.
Crawford et al., Primary T Cell Expansion and Differentiation In Vivo Requires Antigen Presentation by B Cells, J. Immunology, 2006, pp. 3498-3506, vol. 176.
Bar-Or et al., Abnormal B-Cell Cytokine Responses: A Trigger of T-Cell-Mediated Disease in MS?, Annals of Neurology, Apr. 2010, pp. 452-461, vol. 67.
Lisak et al., Secretory Products of Multiple Sclerosis B Cells are Cytotoxic to Oligodendroglia In Vitro, J. Neuroimmunology, 2012, pp. 85-95, vol. 246.
Weber et al., The Role of Antibodies in Multiple Sclerosis, Biochemica et Biophysica Acta, 2011, pp. 239-245, vol. 1812.
Serafini et al., Detection of Ectopic B-Cell Follicles with Germinal Centers in the Meninges of Patients with Secondary Progressive Multiple Sclerosis, Brain Pathology, 2004, pp. 164-174, vol. 14.
Magliozzi et al., A Gradient of Neuronal Loss and Meningeal Inflammation in Multiple Sclerosis, Annals of Neurology, 2010, pp. 477-493, vol. 68.
Bove et al., Evaluating More Naturalistic Outcome Measures: A 1-Year Smartphone Study in Multiple Sclerosis, Neurology: Neuroimmunology & Neuroinflammation, 2015, 10 pgs.
Link et al., Oligoclonal Bands in Multiple Sclerosis Cerebrospinal Fluid: An Update on Methodology and Clinical Usefulness, J. Neuroimmunology, 2006, pp. 17-28, vol. 180.
Tsang et al., Multiple Sclerosis: Diagnosis, Management and Prognosis, Australian Family Physician, Dec. 2011, pp. 948-955, vol. 40.
Compston et al., Multiple Sclerosis, Lancet, Oct. 25, 2008, pp. 1502-1517, vol. 372.
Johnston et al., First-Line Disease-Modifying Therapies in Paediatric Multiple Sclerosis: A Comprehensive Overview, Drugs, 2012, pp. 1195-1211, vol. 72.
Polman et al., Diagnostic Criteria for Multiple Sclerosis: 2010 Revisions to the McDonald Criteria, Annals of Neurology, 2011, pp. 292-302, vol. 69.
Lublin et al., Defining the Clinical Course of Multiple Sclerosis: The 2013 Revisions, Neurology, Jul. 15, 2014, pp. 278-286, vol. 83.
Rai et al., Zee: Zero-Effort Crowdsourcing for Indoor Localization, Proceedings of the 18th Annual International Conference on Mobile Computing and Networking, 2012, 12 pgs.
Alsheikh et al., Deep Activity Recognition Models with Triaxial Accelerometers, Workshops of the Thirtieth AAAI Conference on Artificial Intelligence, 2016, 7 pgs.
Ordóñez et al., Deep Convolutional and LSTM Recurrent Neural Networks for Multimodal Wearable Activity Recognition, Sensors, 2016, 25 pgs.
Mancini et al., ISway: A Sensitive, Valid and Reliable Measure of Postural Control, J. Neuroengineering and Rehabilitation, 2012, 8 pgs.
Hobart et al., The Multiple Sclerosis Impact Scale (MSIS-29) A New Patient-Based Outcome Measure, Brain, 2001, pp. 962-973, vol. 124.
Hutas, Ocrelizumab, A Humanized Monoclonal Antibody against CD20 for Inflammatory Disorders and B-Cell Malignancies, Current Opinion in Investigational Drugs, 2008, pp. 1206-1215, vol. 9.
Kohler et al., Continuous Cultures of Fused Cells Secreting Antibody of Predefined Specificity, Nature, Aug. 7, 1975, pp. 495-497, vol. 256.
International Search Report and Written Opionion of the International Searching Authority, PCT/EP2017/073137, dated Nov. 8, 2017, 8 pgs.
International Preliminary Report on Patentability, PCT/EP2017/073137, dated Mar. 19, 2019, 6 pgs.

* cited by examiner

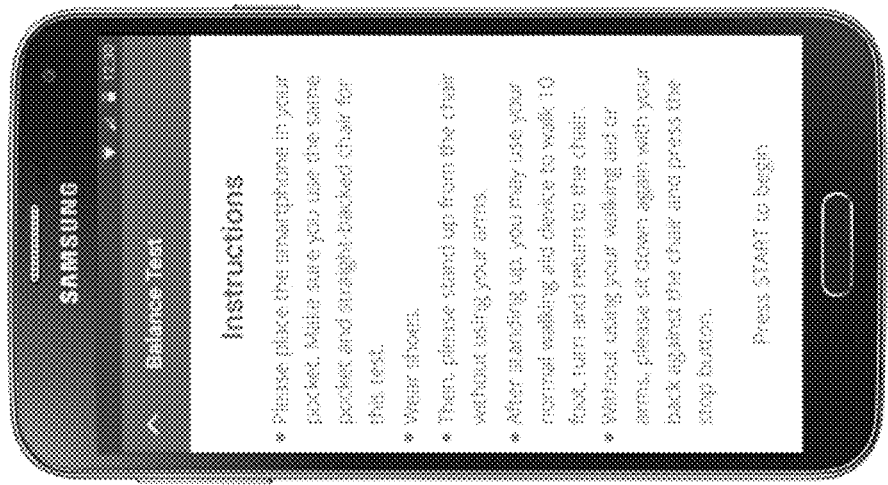
FIG. 2A
FIG. 2B

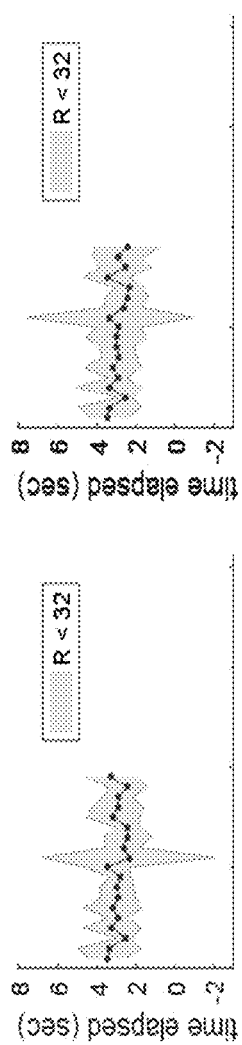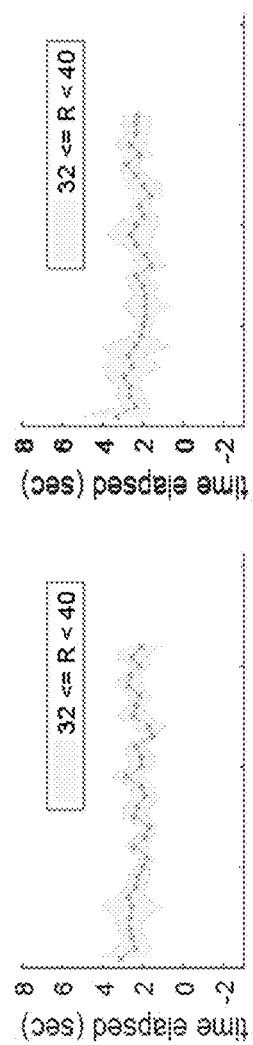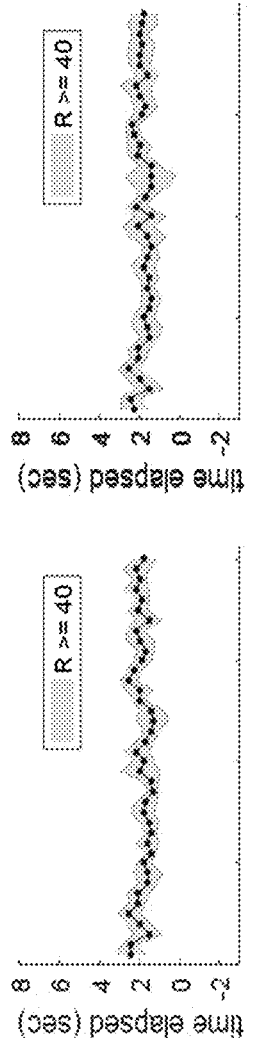

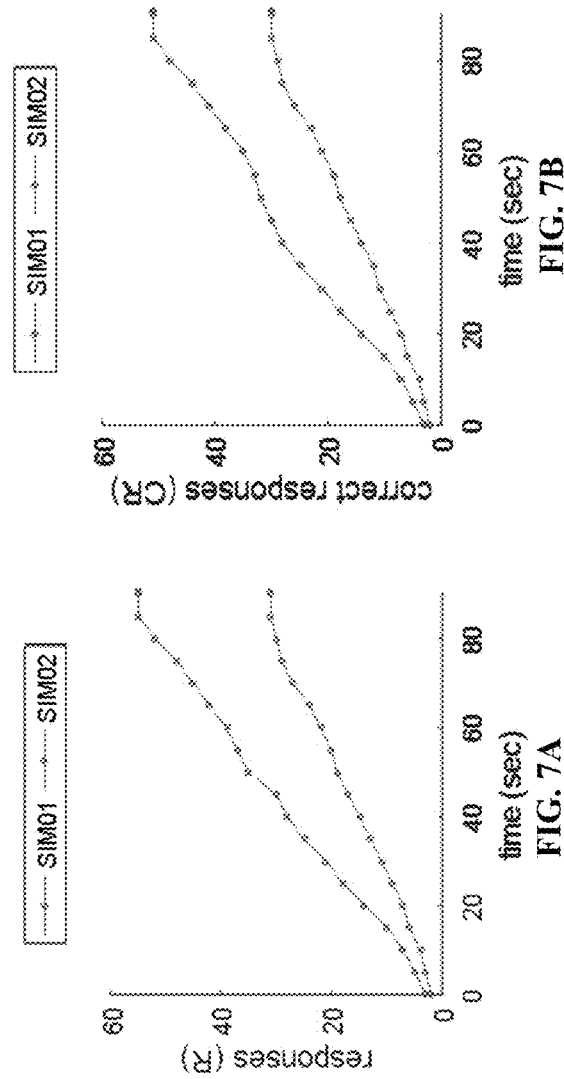
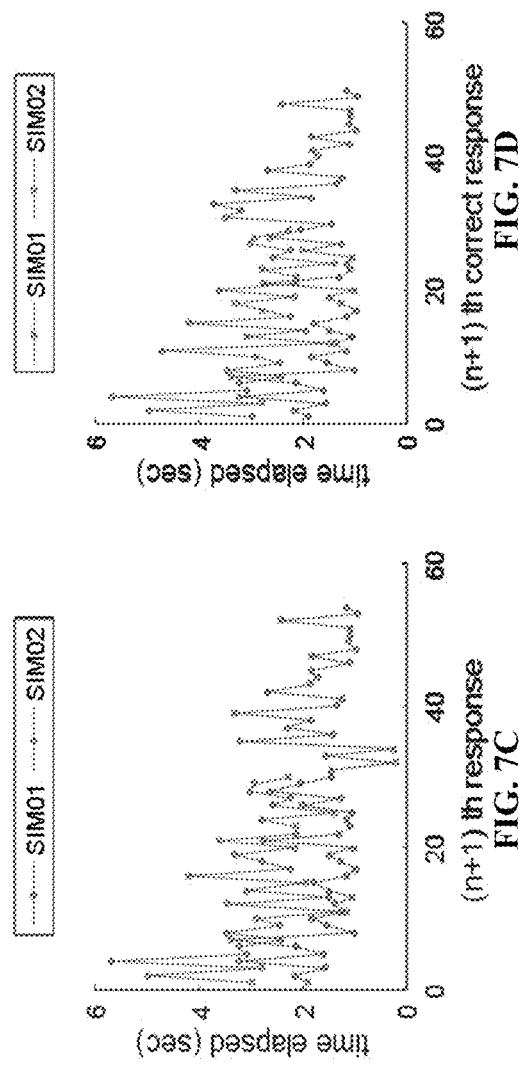

DIGITAL BIOMARKERS FOR PROGRESSING MS

RELATED APPLICATIONS

This application is a continuation of PCT/EP2017/073137, filed Sep. 14, 2017, which claims priority to European Application No. 16 188 849.0, filed Sep. 14, 2016, the disclosures of both of which are hereby incorporated by reference in their entirety.

BACKGROUND

This disclosure relates to the field of diagnostics. Specifically, it relates to a method of identifying progressing multiple sclerosis (MS) in a subject comprising the steps of determining at least one performance parameter determined from a dataset of activity measurements obtained from said subject using a mobile device, and comparing the determined at least one performance parameter to a reference, whereby a subject with progressing MS will be identified. Moreover, encompassed by the present disclosure is a method of recommending an anti-CD20 antibody therapy against MS comprising the steps of the method of the present disclosure and the further step of recommending the anti-CD20 antibody therapy if the subject suffers from progressing MS. The present disclosure also relates to a mobile device comprising a processor, at least one sensor and a database as well as software which is tangibly embedded to said device and, when running on said device, carries out the method of the disclosure as well as the use of such a device for identifying a subject suffering from progressing MS.

Multiple sclerosis (MS) is a severe neurodegenerative disease which at present cannot be cured. Affected by this disease are approximately 2 to 3 million individuals worldwide. It is the most common disease of the central nervous system (CNS) that causes prolonged and severe disability in young adults. There is evidence supporting the concept that a B- and T cell-mediated inflammatory process against self-molecules within the white matter of the brain and spinal cord causes the disease. However, its etiology is still not well understood. It has been found that myelin-reactive T cells are present in both MS patients and healthy individuals. Accordingly, the primary abnormality in MS may involve more likely an impaired regulatory mechanism leading to an enhanced T cell activation status and less stringent activation requirements. The pathogenesis of MS includes activation of encephalitogenic, i.e., autoimmune myelin-specific T cells outside the CNS, followed by an opening of the blood-brain barrier, T cell and macrophage infiltration, microglia activation and demyelination. The latter causes irreversible neuronal damage (see, e.g., Aktas 2005, Neuron 46, 421-432, Zamvil 2003, Neuron 38:685-688).

It was shown more recently that besides T cells, B lymphocytes (expressing CD20 molecule) may play a central role in MS and influence the underlying pathophysiology through at least four specific functions:
1. Antigen presentation: B cells can present self neuroantigens to T cells and activate them (Crawford A, et al. J Immunol 2006; 176(6):3498-506; Bar-Or A, et al. Ann Neurol 2010; 67(4):452-61)
2. Cytokine production: B cells in patients with MS produce abnormal proinflammatory cytokines, which can activate T cells and other immune cells (Bar-Or A, et al. Ann Neurol 2010; 67(4):452-61; Lisak R P, et al. J Neuroimmunol 2012; 246(1-2):85-95)
3. Autoantibody production: B cells produce autoantibodies that may cause tissue damage and activate macrophages and natural killer (NK) cells (Weber M S, et al. Biochim Biophys Acta 2011; 1812(2):239-45)
4. Follicle-like aggregate formation: B cells are present in ectopic lymphoid follicle-like aggregates, linked to microglia activation, local inflammation, and neuronal loss in the nearby cortex (Serafini B, et al. Brain Pathol 2004; 14(2):164-74; Magliozzi R, et al. Ann Neurol 2010; 68(4):477-93)

Although there is sound knowledge about the mechanisms responsible for the encephalitogenicity, far less is known regarding the control mechanisms for regulating harmful lymphocyte responses into and within the CNS in a subject.

MS diagnosis is based at present on clinical investigations by a medical practitioner. Such investigations involve testing of the capabilities of a patient for certain physical activities. Several tests have been developed and are routinely applied by medical practitioners. These tests aim at assessing walking, balance, and other motoric abilities. Examples of currently applied tests are the Expanded Disability Status Scale (EDSS, www.neurostatus.net) or Multiple Sclerosis Functional Composite (MSFC). These tests require the presence of a medical practitioner for evaluation and assessment purposes and are currently performed ambulant at doctor's offices or hospitals. Very recently, there have been some efforts in monitoring MS patients using smartphone devices in order to collect data of MS patients in a natural setting (Bove 2015, Neurol Neuroimmunol Neuroinflamm 2 (6):e162).

Further, diagnostic tools are used in MS diagnosis. Such tools include neuroimaging, analysis of cerebrospinal fluid and evoked potentials. Magnetic resonance imaging (MRI) of the brain and spinal cord can visualize demyelination (lesions or plaques). Contrast agents containing gadolinium can be administered intravenously to mark active plaques and, differentiate acute inflammation from the existence of older lesions which are not associated with symptoms at the moment of the evaluation. The analysis of cerebrospinal fluid obtained from a lumbar puncture can provide evidence of chronic inflammation of the central nervous system. The cerebrospinal fluid can be analyzed for oligoclonal immunoglobulin bands, which are an inflammation marker present in 75-85% of people with MS (Link 2006, J Neuroimmunol. 180 (1-2): 17-28). However, none of the aforementioned techniques is specific to MS. Therefore, ascertainment of diagnosis may require repetition of clinical and MRI investigations to demonstrate dissemination in space and in time of the disease which is a prerequisite to MS diagnosis.

There are several treatments approved by regulatory agencies for relapsing-remitting multiple sclerosis which shall modify the course of the disease. These treatments include interferon beta-1a, interferon beta-1b, glatiramer acetate, mitoxantrone, natalizumab, fingolimod, teriflunomide, dimethyl fumarate, alemtuzumab, and daclizumab. The interferons and glatiramer acetate are first-line treatments that reduce relapses by approximately 30% (see, e.g., Tsang 2011, Australian family physician 40 (12): 948-55). Natalizumab reduces the relapse rate more than the interferons, however, due to issues of adverse effects it is a second-line agent reserved for those who do not respond to other treatments or patients with severe disease (see, e.g., Tsang 2011, loc. cit.). Treatment of clinically isolated syndrome (CIS) with interferons decreases the chance of progressing to clinically definite MS (Compston 2008, Lancet 372 (9648): 1502-17). Efficacy of interferons and glatiramer acetate in children has been estimated to be roughly equivalent to that of adults (Johnston 2012, Drugs 72 (9): 1195-211).

Recently, new monoclonal antibodies such as ocrelizumab, alemtuzumab and daclizumab have shown potential as therapeutics for MS. The anti-CD20 B-cell targeting monoclonal antibody ocrelizumab has shown beneficial effects in both relapsing and primary progressive forms of MS in one phase II and three phase III trials (NCT00676715, NCT01247324, NCT01412333, NCT01194570).

MS is a clinically heterogeneous inflammatory disease of the CNS. Therefore, diagnostic tools are needed that allow a reliable diagnosis and identification of the present disease status and can, thus, aid an accurate treatment, in particular, for those patients suffering from progressing forms of MS.

SUMMARY

The technical problem underlying this disclosure may be seen in the provision of means and methods complying with the aforementioned needs. The technical problem is addressed by the embodiments described herein below.

Thus, the present disclosure relates to a method of identifying progressing multiple sclerosis (MS) in a subject comprising the steps of:
a) determining at least one performance parameter from a dataset of activity measurements obtained from said subject using a mobile device; and
b) comparing the determined at least one performance parameter to a reference, whereby a subject with progressing MS will be identified.

Typically, the method further comprises the step of (c) identifying progressing MS in a subject based on the comparison carried out in step (b).

In some embodiments, the method may also comprise prior to step (a) the step of obtaining from the subject using a mobile device a dataset of activity measurements during predetermined activity performed by the subject. However, typically the method is an ex vivo method carried out on an existing dataset of activity measurements of a subject which does not require any physical interaction with the said subject.

The method as referred to in accordance with the present disclosure includes a method which essentially consists of the aforementioned steps or a method which may include additional steps.

The method may be carried out on the mobile device by the subject once the dataset of activity measurements has been acquired. Thus, the mobile device and the device acquiring the dataset may be physically identical, i.e., the same device. Such a mobile device shall have a data acquisition unit which typically comprises means for data acquisition, i.e., means which detect or measure either quantitatively or qualitatively physical and/or chemical parameters and transform them into electronic signals transmitted to the evaluation unit in the mobile device used for carrying out the method. The data acquisition unit comprises means for data acquisition, i.e., means which detect or measure either quantitatively or qualitatively physical and/or chemical parameters and transform them into electronic signals transmitted to the device being remote from the mobile device and used for carrying out the method according to the disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used as means for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, sweat analysis sensors and the like. The evaluation unit typically comprises a processor and a database as well as software which is tangibly embedded to said device and, when running on said device, carries out the method of the disclosure. More typically, such a mobile device may also comprise a user interface, such as a screen, which allows for providing the result of the analysis carried out by the evaluation unit to a user.

Alternatively, it may be carried out on a device being remote with respect to the mobile device that has been used to acquire the said dataset. In this case, the mobile device shall merely comprise means for data acquisition, i.e., means which detect or measure either quantitatively or qualitatively physical and/or chemical parameters and transform them into electronic signals transmitted to the device being remote from the mobile device and used for carrying out the method according to this disclosure. Typically, said means for data acquisition comprise at least one sensor. It will be understood that more than one sensor can be used in the mobile device, i.e., at least two, at least three, at least four, at least five, at least six, at least seven, at least eight, at least nine or at least ten or even more different sensors. Typical sensors used as means for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, sweat analysis sensors and the like. Thus, the mobile device and the device used for carrying out the method of this disclosure may be physically different devices. In this case, the mobile device may correspond with the device used for carrying out the method of the present disclosure by any means for data transmission. Such data transmission may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Accordingly, for carrying out the method of the present disclosure, the only requirement is the presence of a dataset of activity measurements obtained from a subject using a mobile device. The said dataset may also be transmitted or stored from the acquiring mobile device on a permanent or temporary memory device which subsequently can be used to transfer the data to the device used for carrying out the method of this disclosure. The remote device which carries out the method of the disclosure in this setup typically comprises a processor and a database as well as software which is tangibly embedded to said device and, when running on said device, carries out the disclosed method. More typically, the said device may also comprise a user interface, such as a screen, which allows for providing the result of the analysis carried out by the evaluation unit to a user.

The term "identifying" as used herein refers to assessing whether a subject suffers from progressing MS, or not. As will be understood by those skilled in the art, such an assessment, although preferred to be, may usually not be correct for 100% of the investigated subjects. The term, however, requires that a statistically significant portion of subjects can be correctly assessed and, thus, identified as suffering from progressing MS. Whether a portion is statistically significant can be determined without further ado by the person skilled in the art using various well known statistical evaluation tools, e.g., determination of confidence intervals, p-value determination, Student's t-test, Mann-Whitney test, etc. Details may be found in Dowdy and Wearden, Statistics for Research, John Wiley & Sons, New York 1983. Typically envisaged confidence intervals are at least 50%, at least 60%, at least 70%, at least 80%, at least 90%, at least 95%. The p-values are, typically, 0.2, 0.1, 0.05. Thus, the method of the present disclosure, typically, aids the identification of progressing MS by providing a means for evaluating a dataset of activity measurements.

The term "multiple sclerosis (MS)" as used herein relates to disease of the central nervous system (CNS) that typically causes prolonged and severe disability in a subject suffering therefrom. There are four standardized subtype definitions of MS which are also encompassed by the term as used in accordance with this disclosure: relapsing-remitting, secondary progressive, primary progressive and progressive relapsing. The term relapsing forms of MS is also used and encompasses relapsing-remitting and secondary progressive MS with superimposed relapses. The relapsing-remitting subtype is characterized by unpredictable relapses followed by periods of months to years of remission with no new signs of clinical disease activity. Deficits suffered during attacks (active status) may either resolve or leave sequelae. This describes the initial course of 85 to 90% of subjects suffering from MS. Secondary progressive MS describes those with initial relapsing-remitting MS, who then begin to have progressive neurological decline between acute attacks without any definite periods of remission. Occasional relapses and minor remissions may appear. The median time between disease onset and conversion from relapsing remitting to secondary progressive MS is about 19 years. The primary progressive subtype describes about 10 to 15% of subjects who never have remission after their initial MS symptoms. It is characterized by progressive of disability from onset, with no, or only occasional and minor, remissions and improvements. The age of onset for the primary progressive subtype is later than other subtypes. Progressive relapsing MS describes those subjects who, from onset, have a steady neurological decline but also suffer clear superimposed attacks. It is now accepted that this latter progressive relapsing phenotype is a variant of primary progressive MS (PPMS) and diagnosis of PPMS according to McDonald 2010 criteria includes the progressive relapsing variant.

Symptoms associated with MS include changes in sensation (hypoesthesia and par-aesthesia), muscle weakness, muscle spasms, difficulty in moving, difficulties with coordination and balance (ataxia), problems in speech (dysarthria) or swallowing (dysphagia), visual problems (nystagmus, optic neuritis and reduced visual acuity, or diplopia), fatigue, acute or chronic pain, bladder, sexual and bowel difficulties. Cognitive impairment of varying degrees as well as emotional symptoms of depression or unstable mood are also frequent symptoms. The main clinical measure of disability progression and symptom severity is the Expanded Disability Status Scale (EDSS). Further symptoms of MS are well known in the art and are described in the standard text books of medicine and neurology, such as for instance Bradley W G, et al. Neurology in Clinical Practice (5th ed. 2008).

The term "progressing MS" as used herein refers to a condition, where the disease and/or one or more of its symptoms get worse over time. Typically, the progression is accompanied by the appearance of active statuses. The said progression may occur in all subtypes of the disease. However, typically "progressing MS" shall be determined in accordance with the present disclosure in subjects suffering from relapsing-remitting MS.

However, the method of the present disclosure can be applied, in particular, in the context of:
Identifying clinical disease activity (i.e., relapse occurrence),
disability progression,
primary progressive MS disease course, as defined by established consensus criteria such as but not exclusively the McDonald Criteria 2010 (Polman 2011, Ann Neurol 69:292-302), and/or the Lublin et al. criteria 2013 (Lublin 2014, Neurology 83: 278-286),
secondary progressive MS disease course, as defined by established consensus criteria such as but not exclusively the McDonald Criteria 2010 (Polman loc. cit.), and/or the Lublin et al. criteria 2013 (Lublin loc. cit.),
primary progressive MS, as defined by established consensus criteria such as but not exclusively the McDonald Criteria 2010 (Polman loc. cit.), and/or the Lublin et al. criteria 2013 (Lublin loc. cit.), and/or
secondary progressive MS, as defined by established consensus criteria such as but not exclusively the McDonald Criteria 2010 (Polman loc. cit.), and/or the Lublin et al. criteria 2013 (Lublin loc. cit.).

Moreover, it is suitable for risk assessments in MS patients and, in particular for:
Risk prediction models estimating probabilities of disease activity (i.e., relapse and/or new or enlarging lesions on T2 or FLAIR (Fluid Attenuating Inversion Recovery) weighted brain or spinal cord MRI, and/or gadolinium-enhancing lesions on brain or spinal cord MRI),
risk prediction models estimating probabilities of disability progression in patients with a diagnosis of multiple sclerosis (MS), as measured for instance but not exclusively by the Expanded Disability Status Scale neurostatus (EDSS), the Multiple Sclerosis Functional Composite (MSFC), and its components the Timed 25 foot walk test or the 9-hole peg test,
risk prediction models estimating probabilities of emergence of secondary progressive MS disease course in relapsing-onset MS as defined by established consensus criteria such as but not exclusively the McDonald Criteria 2010 (Polman loc. cit.), and/or the Lublin et al. criteria 2013 (Lublin loc. cit.), and/or
risk prediction models estimating probabilities of emergence of specific MRI signs of primary or secondary progressive MS disease course as defined for instance but not exclusively by the presence of slowly expanding lesions (SELs) on T2 or FLAIR weighted brain or spinal cord MM, or signs of meningeal inflammation detected on FLAIR-weighted brain or spinal cord MRI after injection of gadolinium-based contrast agents.

Furthermore, the method can be applied in the context of:
Developing algorithmic solutions using for instance machine-learning and pattern recognition techniques to estimate probabilities of disease-modifying treatment (DMT) response or failure as evaluated by the risk of ongoing disease activity (i.e., relapse and/or new or enlarging lesions on T2 or FLAIR weighted brain or spinal cord MRI, and/or gadolinium-enhancing lesions on brain or spinal cord MRI) in patients with a diagnosis of multiple sclerosis (MS) treated with specific DMTs,
developing algorithmic solutions using for instance machine-learning and pattern recognition techniques to estimate probabilities of DMT response or failure as evaluated by the risk of ongoing disability progression in patients with a diagnosis of multiple sclerosis (MS) treated with specific DMTs, as measured for instance but not exclusively by the Expanded Disability Status Scale (EDSS), the Timed 25 foot walk test or the 9-hole peg test, and/or developing algorithmic solutions using for instance machine-learning and pattern recognition techniques to estimate probabilities of DMT response or failure as evaluated by the risk of worsening in brain MRI measures of neural tissue damage and neurodegeneration such as but not exclusively the whole brain volume, brain parenchymal fraction, whole grey matter volume, cortical grey matter volume, volume of specific cortical areas, deep grey matter volume, thalamic volume, corpus callosum surface, white matter volume, third ventricle volume, total brain T2 lesion volume, total brain T1 lesion volume, total brain FLAIR lesion volume in patients with a diagnosis of multiple sclerosis (MS) treated with specific DMTs, and/or algorithmic solutions using for instance machine-learning and pattern recognition techniques to estimate probabilities of emergence of secondary progressive MS disease course in relapsing-onset MS as defined by established consensus criteria such as but not exclusively the McDonald Criteria 2010 (Polman loc. cit.), and/or the Lublin et al. criteria 2013 (Lublin loc. cit.).

The term "subject" as used herein relates to animals and, typically, to mammals. In particular, the subject is a primate and, most typically, a human. The subject in accordance with the present disclosure shall suffer from or shall be suspected to suffer from MS, i.e., it may already show some or all of the symptoms associated with the said disease.

The term "at least one" means that one or more performance parameters may be determined in accordance with the disclosure, i.e., at least two, at least three, at least four, at least five, at least six, at least seven, at least eight, at least nine or at least ten or even more different performance parameters. Thus, there is no upper limit for the number of different performance parameters which can be determined in accordance with the method of this disclosure. Typically, however, there will be between one and three different performance parameters per dataset of activity measurement determined.

The term "performance parameter" as used herein refers to a parameter which is indicative for the capability of a subject to perform a certain physical or cognitive activity, in particular, it is a parameter indicative for the subject's motoric and/or fine motoric capabilities and function, walking, color vision, attention, dexterity and/or cognitive capabilities, quality of life, fatigue, mental state, mood, vision and/or cognition. Depending on the type of activity which is measured, the performance parameter can be derived from the dataset acquired by the activity measurement performed on the subject. Such performance parameters may be based on the time which is required to perform a certain activity, e.g., it may be the velocity or frequency with which a certain activity is performed or it may be the duration of the gap between activities. Further, it may be based on the accuracy with which a task is performed or may be based on the amount of task that can be performed. Particular performance parameters to be used in accordance with the present disclosure depend on the measured activity and are listed elsewhere herein in more detail.

The term "dataset of activity measurements" refers to the entirety of data which has been acquired by the mobile device from a subject during activity measurements or any subset of said data useful for deriving the performance parameter. Activities to be performed and measured by the mobile device during performance are performing a Symbol Digit Modalities Test (SDMT), performing active walking tests, in particular, the 2-Minute Walking Test (2MWT) and the Five U-Turn Test (5UTT), passive continuous analysis of gait (CAG), performing orthostatic posture and balance tests, in particular, the Static Balance Test (SBT), performing fine motoric activities, in particular, the Draw a Shape and/or Squeeze a Shape tests described elsewhere herein in detail, answering mood scale questions, answering questions on quality of life and MS symptoms, in particular, by performing the 29-Item Multiple Sclerosis Impact Scale (MSIS29) questionnaire (version 2 or subsequent iterations) and/or the Multiple Sclerosis Symptom Tracker (MSST). Moreover, the dataset of activity measurements may be obtained from a passive monitoring of all or a predetermined subset of activities of a subject performed during a certain time window, e.g., during daily routine. These measurements allow for assessing a subject's quality of life, fatigue, mental state and/or mood. In this context, passive monitoring may include continuous measurements of gait, the amount of movement in daily routines in general, e.g., frequency and/or velocity of walking, the types of movement in daily routines, e.g., amount, ability and/or velocity to stand up/sit down, stand still and balance, general mobility in daily living as indicated by, e.g., visiting more or fewer locations, changes in moving behavior as indicated by, e.g., changes in types of locations visited.

In the following, particular envisaged activity tests and means for measuring by a mobile device in accordance with the disclosed method are specified:

(1) A computer-implemented (electronic) Symbol Digit Modalities Test (eSDMT).

In an embodiment, the mobile device is, thus, adapted for performing or acquiring a data from an electronic Symbol Digit Modalities Test (eSDMT). The conventional paper SDMT version of the test consists of a sequence of 120 symbols to be displayed in a maximum 90 seconds and a reference key legend (3 versions are available) with 9 symbols in a given order and their respective matching digits from 1 to 9. The smartphone-based eSDMT is meant to be self-administered by patients and will use a sequence of symbols, typically, the same sequence of 110 symbols, and a random alternation (form one test to the next) between reference key legends, typically, the 3 reference key legends, of the paper/oral version of SDMT. The eSDMT similarly to the paper/oral version measures the speed (number of correct paired responses) to pair abstract symbols with specific digits in a predetermined time window, such as 90 seconds time. The test is, typically, performed weekly but could alternatively be performed at higher (e.g., daily) or lower (e.g., bi-weekly) frequency. The test could also alternatively encompass more than 110 symbols and more and/or evolutionary versions of reference key legends. The symbol sequence could also be administered randomly or according to any other modified pre-specified sequence.

Typical eSDMT performance parameters of interest:
1. Number of correct responses
   a. Total number of overall correct responses (CR) in 90 seconds (similar to oral/paper SDMT)
   b. Number of correct responses from time 0 to 30 seconds ($CR_{0-30}$)
   c. Number of correct responses from time 30 to 60 seconds ($CR_{30-60}$)

d. Number of correct responses from time 60 to 90 seconds ($CR_{60-90}$)
e. Number of correct responses from time 0 to 45 seconds ($CR_{0-45}$)
f. Number of correct responses from time 45 to 90 seconds ($CR_{45-90}$)
g. Number of correct responses from time i to j seconds ($CR_{i-j}$), where i,j are between 1 and 90 seconds and i<j 2. Number of errors
a. Total number of errors (E) in 90 seconds
b. Number of errors from time 0 to 30 seconds ($E_{0-30}$)
c. Number of errors from time 30 to 60 seconds ($E_{30-60}$)
d. Number of errors from time 60 to 90 seconds ($E_{60-90}$)
e. Number of errors from time 0 to 45 seconds ($E_{0-45}$)
f. Number of errors from time 45 to 90 seconds ($E_{45-90}$)
g. Number of errors from time i to j seconds ($E_{i-j}$), where i,j are between 1 and 90 seconds and i<j 3. Number of responses
a. Total number of overall responses (R) in 90 seconds
b. Number of responses from time 0 to 30 seconds ($R_{0-30}$)
c. Number of responses from time 30 to 60 seconds ($R_{30-60}$)
d. Number of responses from time 60 to 90 seconds ($R_{60-90}$)
e. Number of responses from time 0 to 45 seconds ($R_{0-45}$)
f. Number of responses from time 45 to 90 seconds ($R_{45-90}$)

4. Accuracy rate
a. Mean accuracy rate (AR) over 90 seconds: $AR=CR/R$
b. Mean accuracy rate (AR) from time 0 to 30 seconds: $AR_{0-30}=CR_{0-30}/R_{0-30}$
c. Mean accuracy rate (AR) from time 30 to 60 seconds: $AR_{30-60}=CR_{30-60}/R_{30-60}$
d. Mean accuracy rate (AR) from time 60 to 90 seconds: $AR_{60-90}=CR_{60-90}/R_{60-90}$
e. Mean accuracy rate (AR) from time 0 to 45 seconds: $AR_{0-45}=CR_{0-45}/R_{0-45}$
f. Mean accuracy rate (AR) from time 45 to 90 seconds: $AR_{45-90}=CR_{45-90}/R_{45-90}$ 5. End of task fatigability indices
a. Speed Fatigability Index (SFI) in last 30 seconds: $SFI_{60-90}=CR_{60-90}/\max(CR_{0-30}, CR_{30-60})$
b. SFI in last 45 seconds: $SFI_{45-90}=CR_{45-90}/CR_{0-45}$
c. Accuracy Fatigability Index (AFI) in last 30 seconds: $AFI_{60-90}=AR_{60-90}/\max(AR_{0-30}, AR_{30-60})$
d. AFI in last 45 seconds: $AFI_{45-90}=AR_{45-90}/AR_{0-45}$ 6. Longest sequence of consecutive correct responses
a. Number of correct responses within the longest sequence of overall consecutive correct responses (CCR) in 90 seconds
b. Number of correct responses within the longest sequence of consecutive correct responses from time 0 to 30 seconds ($CCR_{0-30}$)
c. Number of correct responses within the longest sequence of consecutive correct responses from time 30 to 60 seconds ($CCR_{30-60}$)
d. Number of correct responses within the longest sequence of consecutive correct responses from time 60 to 90 seconds ($CCR_{60-90}$)
e. Number of correct responses within the longest sequence of consecutive correct responses from time 0 to 45 seconds ($CCR_{0-45}$)
f. Number of correct responses within the longest sequence of consecutive correct responses from time 45 to 90 seconds ($CCR_{45-90}$)

7. Timegap between responses
a. Continuous variable analysis of gap (G) time between two successive responses
b. Maximal gap (GM) time elapsed between two successive responses over 90 seconds
c. Maximal gap time elapsed between two successive responses from time 0 to 30 seconds ($GM_{0-30}$)
d. Maximal gap time elapsed between two successive responses from time 30 to 60 seconds ($GM_{30-60}$)
e. Maximal gap time elapsed between two successive responses from time 60 to 90 seconds ($GM_{60-90}$)
f. Maximal gap time elapsed between two successive responses from time 0 to 45 seconds ($GM_{0-45}$)
g. Maximal gap time elapsed between two successive responses from time 45 to 90 seconds ($GM_{45-90}$)

8. Time Gap between correct responses
a. Continuous variable analysis of gap (Gc) time between two successive correct responses
b. Maximal gap time elapsed between two successive correct responses (GcM) over 90 seconds
c. Maximal gap time elapsed between two successive correct responses from time 0 to 30 seconds ($GcM_{0-30}$)
d. Maximal gap time elapsed between two successive correct responses from time 30 to 60 seconds ($GcM_{30-60}$)
e. Maximal gap time elapsed between two successive correct responses from time 60 to 90 seconds ($GcM_{60-90}$)
f. Maximal gap time elapsed between two successive correct responses from time 0 to 45 seconds ($GcM_{0-45}$)
g. Maximal gap time elapsed between two successive correct responses from time 45 to 90 seconds ($GcM_{45-90}$)

9. Fine finger motor skill function parameters captured during eSDMT
a. Continuous variable analysis of duration of touchscreen contacts (Tts), deviation between touchscreen contacts (Dts) and center of closest target digit key, and mistyped touchscreen contacts (Mts) (i.e., contacts not triggering key hit or triggering key hit but associated with secondary sliding on screen), while typing responses over 90 seconds
b. Respective variables by epochs from time 0 to 30 seconds: $Tts_{0-30}$, $Dts_{0-30}$, $Mts_{0-30}$
c. Respective variables by epochs from time 30 to 60 seconds: $Tts_{30-60}$, $Dts_{30-60}$, $Mts_{30-60}$
d. Respective variables by epochs from time 60 to 90 seconds: $Tts_{60-90}$, $Dts_{60-90}$, $Mts_{60-90}$
e. Respective variables by epochs from time 0 to 45 seconds: $Tts_{0-45}$, $Dts_{0-45}$, $Mts_{0-45}$
f. Respective variables by epochs from time 45 to 90 seconds: $Tts_{45-90}$, $DtS_{45-90}$, $MtS_{45-90}$ 10. Symbol-specific analysis of performances by single symbol or cluster of symbols
a. CR for each of the 9 symbols individually and all their possible clustered combinations
b. AR for each of the 9 symbols individually and all their possible clustered combinations
c. Gap time (G) from prior response to recorded responses for each of the 9 symbols individually and all their possible clustered combinations
d. Pattern analysis to recognize preferential incorrect responses by exploring the type of mistaken substitutions for the 9 symbols individually and the 9 digit responses individually 11. Learning and cognitive reserve analysis
a. Change from baseline (baseline defined as the mean performance from the first 2 administrations of the test)

in CR (overall and symbol-specific as described in #9) between successive administrations of eSDMT
b. Change from baseline (baseline defined as the mean performance from the first 2 administrations of the test) in AR (overall and symbol-specific as described in #9) between successive administrations of eSDMT
c. Change from baseline (baseline defined as the mean performance from the first 2 administrations of the test) in mean G and GM (overall and symbol-specific as described in #9) between successive administrations of eSDMT
d. Change from baseline (baseline defined as the mean performance from the first 2 administrations of the test) in mean Gc and GcM (overall and symbol-specific as described in #9) between successive administrations of eSDMT
e. Change from baseline (baseline defined as the mean performance from the first 2 administrations of the test) in $SFI_{60-90}$ and $SFI_{45-90}$ between successive administrations of eSDMT
f. Change from baseline (baseline defined as the mean performance from the first 2 administrations of the test) in $AFI_{60-90}$ and $AFI_{45-90}$ between successive administrations of eSDMT
g. Change from baseline (baseline defined as the mean performance from the first 2 administrations of the test) in Tts between successive administrations of eSDMT
h. Change from baseline (baseline defined as the mean performance from the first 2 administrations of the test) in Dts between successive administrations of eSDMT
i. Change from baseline (baseline defined as the mean performance from the first 2 administrations of the test) in Mts between successive administrations of eSDMT (2) A sensor-based (e.g., accelerometer, gyroscope, magnetometer, global positioning system [GPS]) and computer implemented test for measures of ambulation performance and gait and stride dynamics, in particular, the 2-Minute Walking Test (2MWT) and the Five U-Turn Test (5UTT), and test for ambulation performance, step/stride dynamics, and upper limb motor function while walking using data collected from passive Continuous Analysis of Gait (CAG).

In one embodiment, the mobile device is adapted to perform or acquire data from the Two-Minute Walking Test (2MWT). The aim of this test is to assess difficulties, fatigability or unusual patterns in long-distance walking by capturing gait features in a two-minute walk test (2MWT). Data will be captured from the mobile device. A decrease of stride and step length, increase in stride duration, increase in step duration and asymmetry and less periodic strides and steps may be observed in case of disability progression or emerging relapse. Arm swing dynamic while walking will also be assessed via the mobile device. The subject will be instructed to "walk as fast and as long as you can for 2 minutes but walk safely." The 2MWT is a simple test that is required to be performed indoor or outdoor, on even ground in a place where patients have identified they could walk straight for as far as ≥200 meters without U-turns. Subjects are allowed to wear regular footwear and an assistive device and/or orthotic as needed. The test is typically performed daily.

Typical 2MWT performance parameters of particular interest:
1. Surrogate of walking speed and spasticity:
    a. Total number of steps detected in, e.g., 2 minutes (ΣS)
    b. Total number of rest stops if any detected in 2 minutes (ΣRs)
    c. Continuous variable analysis of walking step time (WsT) duration throughout the 2MWT
    d. Continuous variable analysis of walking step velocity (WsV) throughout the 2MWT (step/second)
    e. Step asymmetry rate throughout the 2MWT (mean difference of step duration between one step to the next divided by mean step duration): $SAR=mean\Delta(WsT_x-WsT_{x+1})/(120/\Sigma S)$
    f. Total number of steps detected for each epoch of 20 seconds ($\Sigma S_{t, t+20}$)
    g. Mean walking step time duration in each epoch of 20 seconds: $WsT_{t, t+20}=20/\Sigma S_{t, t+20}$
    h. Mean walking step velocity in each epoch of 20 seconds: $WsV_{t,t+20}=\Sigma S_{t, t+20}/20$
    i. Step asymmetry rate in each epoch of 20 seconds: $SAR_{t, t+20}=mean\Delta_{t, t+20}(WsT_x-WsT_{x+1})/(20/\Sigma S_{t, t+20})$
    j. Step length and total distance walked through biomechanical modelling
2. Walking fatigability indices:
    a. Deceleration index: $DI=WsV_{100-120}/max (WsV_{0-20}, WsV_{20-40}, WsV_{40-60})$
    b. Asymmetry index: $AI=SAR_{100-120}/min (SAR_{0-20}, SAR_{20-40}, SAR_{40-60})$ In another embodiment, the mobile device is adapted to perform or acquire data from the Five U-Turn Test (5UTT). The aim of this test is to assess difficulties or unusual patterns in performing U-turns while walking on a short distance at comfortable pace. The 5UTT is required to be performed indoor or outdoor, on even ground where patients are instructed to "walk safely and perform five successive U-turns going back and forward between two points a few meters apart." Gait feature data (change in step counts, step duration and asymmetry during U-turns, U-turn duration, turning speed and change in arm swing during U-turns) during this task will be captured by the mobile device. Subjects are allowed to wear regular footwear and an assistive device and/or orthotic as needed. The test is typically performed daily.

Typical 5UTT performance parameters of interest:
1. Mean number of steps needed from start to end of complete U-turn (ΣSu)
2. Mean time needed from start to end of complete U-turn (Tu)
3. Mean walking step duration: $Tsu=Tu/\Sigma Su$
4. Turn direction (left/right)
5. Turning speed (degrees/sec)

In yet another embodiment, the mobile device is adapted for performing or acquiring data from Continuous Analysis of Gait (CAG). Continuous recording of gait feature data (step counts, duration, and asymmetry, as well as arm swing dynamic while walking) captured from sensors will allow passive monitoring of daily volume & quality of walking dynamics. Activity detection is a prior step to gait detection & analysis and activity analysis. It may be based on different more or less complex approaches (Rai 2012, Zee: zero-effort crowdsourcing for indoor localization. Proceedings of the 18th annual international conference on Mobile computing and networking. ACM; Alsheikh, M. A., Selim, A., Niyato, D., Doyle, L., Lin, S., & Tan, H.-P. (2015). Deep Activity Recognition Models with Triaxial Accelerometers. arXiv preprint arXiv:1511.04664; or Ordóñez, F. J., & Roggen, D. (2016). Deep Convolutional and LSTM Recurrent Neural Networks for Multimodal Wearable Activity Recognition. Sensors, 16(1), 115), which considers windows of one second as active if the standard deviation of the accelerometer signal is above 0.01 g. The test is typically performed daily.

Typical CAG performance parameters of interest:
Surrogate of daily walking range and speed:
a. Total number of steps detected for each day of active recording ($\Sigma Sd$)
b. Total cumulative time of detected walking for each day of active recording ($\Sigma T$)
c. Total number of intervals of continuous walking for each day of active recording ($\Sigma Id$)
d. Frequency distribution of the number of steps detected within each interval of continuous walking for each day of active recording ($\Delta Si$)
e. Maximal number of steps in a single interval of continuous walking for each day of active recording (Scmax)
f. Mean walking step time duration for each day of active recording: $WsT = \Sigma T / \Sigma Sd$
g. Mean walking step velocity for each day of active recording: $WsV = \Sigma Sd / \Sigma T$ (step/min)
h. Step length and total distance walked per day derived through biomechanical modelling
i. Variables #a-h by time of the day (3) A sensor-based (e.g., accelerometer, gyroscope, magnetometer) and computer-implemented test for measures of orthostatic posture and balance, in particular, the Static Balance Test (SBT).

In one embodiment, the mobile device is adapted for performing or acquiring data from the Static Balance Test (SBT). The aim of this test is to assess a subject's static balance function as in one of the items (i.e., standing unsupported) of the widely used Berg Balance Scale (BBS), which is a 14-item objective measure designed to assess static balance and fall risk in adult populations. Data will be captured from smartphone and smartwatch sensors. The subjects are asked to stand still unsupported for 30 seconds with relaxed arms straight alongside the body if possible and with the smartphone in his/her pocket. Individuals with increased risk of falling and/or impaired static balance function, may demonstrate altered postural control [sway] and abnormal arm movements. The test is typically performed daily.

Typical SBT performance parameters of interest:
1. Sway jerkiness: time derivative of acceleration (Mancini M et al. J Neuroeng Rehabil. 2012; 22: 9:59)
2. Sway path: total length of trajectory
3. Sway range (4) A computer-implemented test evaluating fine motoric capabilities (fine motoric assessments), in particular, hand motor functions and, in particular, the touchscreen-based "Draw a Shape" and "Squeeze a Shape" tests.

In yet another embodiment, the mobile device is adapted to perform or acquire data from fine motoric assessments and, in particular, Hand Motor Function Tests. Manual dexterity (hand motor function) characterizes an individual's ability to coordinate movement of the hand and fingers and manipulate objects in a timely manner. Manual dexterity greatly impacts a subject's performance in daily activities, completing work related tasks, and engaging in leisure activities.

Manual dexterity was identified in 2007 as a core construct for inclusion in the National Institutes of Health Toolbox (NIH) Toolbox for the assessment of neurological and behavioral Function, as part of the NIH Blueprint for Neuroscience Research initiative, which developed brief yet comprehensive instruments to measure motor, cognitive, sensory, and emotional function. After reviewing existing measures, experts recommended two candidate measures of manual dexterity: 1) 9-Hole Peg Test (9HPT), and 2) Grooved Pegboard Test (GPT) for potential inclusion in the NIH Toolbox because of their applicability across the life span, psychometric soundness, brevity (completion time for one trial is relatively short), and applicability in diverse settings.

Primarily, the 9HPT was selected because it met the most inclusion criteria and the test was easy to administer in all age groups, especially younger children. The time to administer the 9-hole peg test was brief (<5 min to measure for both hands) as required for inclusion in the NIH Toolbox. Existing literature supported 9HPT as a reliable and valid measure of finger dexterity, and as capable for assessing hand dexterity in various diagnostic groups (i.e., multiple sclerosis, stroke, cerebral palsy, cerebellar impairment, and Parkinson's disease).

Normative data for the 9HPT have been published across the age span including children and elderly adults and since the late 90s 9HPT represents the key component of functional upper limb assessment from the Multiple Sclerosis Functional Composite (MSFC) scale.

Moreover, in accordance with this disclosure, two touchscreen-based application tests "Draw a Shape" and "Squeeze a Shape" were developed that aimed at replicating on a user-friendly mobile device interface the characteristics of 9HPT and GPT for enabling remote self-assessment of hand motor function in neurological disorders. The "Draw a Shape" and "Squeeze a Shape" tests will evaluate upper limb motor function and manual dexterity (pinching, drawing) and will be sensitive to change and abnormalities in pyramidal, extrapyramidal, sensory and cerebellar components of upper limb nervous system but also to neuromuscular and myogenic alteration of upper limb function. The test is, typically, performed daily but could alternatively be performed at lower (e.g., weekly or bi-weekly) frequency.

The aim of the "Draw a Shape" test is to assess fine finger control and stroke sequencing. The test is considered to cover the following aspects of impaired hand motor function: tremor and spasticity and impaired hand-eye coordination. The patients are instructed to hold the mobile device in the untested hand and draw on a touchscreen of the mobile device 6 pre-written alternating shapes of increasing complexity (linear, rectangular, circular, sinusoidal, and spiral; see below) with the second finger of the tested hand "as fast and as accurately as possible" within a maximum time of for instance 30 seconds. To draw a shape successfully the patient's finger has to slide continuously on the touchscreen and connect indicated start and end points passing through all indicated check points and keeping within the boundaries of the writing path as much as possible. The patient has maximum two attempts to successfully complete each of the 6 shapes. The test will be alternatingly performed with right and left hand. The user will be instructed on daily alternation. The two linear shapes have each a specific number "a" of checkpoints to connect, i.e "a-1" segments. The square shape has a specific number "b" of checkpoints to connect, i.e., "b-1" segments. The circular shape has a specific number "c" of checkpoints to connect, i.e., "c-1" segments. The eight-shape has a specific number "d" of checkpoints to connect, i.e "d-1" segments. The spiral shape has a specific number "e" of checkpoints to connect, "e-1" segments. Completing the 6 shapes, then, requires successfully drawing a total of "(2a+b+c+d+e-6)" segments.

Typical Draw a Shape test performance parameters of interest:

Based on shape complexity, the linear and square shapes can be associated with a weighting factor (Wf) of 1, circular and sinusoidal shapes a weighting factor of 2, and the spiral shape a weighting factor of 3. A shape which is successfully completed on the second attempt can be associated with a weighting factor of 0.5. These weighting factors are numerical examples which can be changed in the context of the present disclosure.

1. Shape completion performance scores:
   a. Number of successfully completed shapes (0 to 6) ($\Sigma Sh$) per test
   b. Number of shapes successfully completed at first attempt (0 to 6) ($\Sigma Sh_1$)
   c. Number of shapes successfully completed at second attempt (0 to 6) ($\Sigma Sh_2$)
   d. Number of failed/uncompleted shapes on all attempts (0 to 12) ($\Sigma F$)
   e. Shape completion score reflecting the number of successfully completed shapes adjusted with weighting factors for different complexity levels for respective shapes (0 to 10) ($\Sigma[Sh*Wf]$)
   f. Shape completion score reflecting the number of successfully completed shapes adjusted with weighting factors for different complexity levels for respective shapes and accounting for success at first vs. second attempts (0 to 10) ($\Sigma[Sh_1*Wf]+\Sigma[Sh_2*Wf*0.5]$)
   g. Shape completion scores as defined in 1(e), and 1(f) may account for speed at test completion if being multiplied by 30/t, where t would represent the time in seconds to complete the test
   h. Overall and first attempt completion rate for each 6 individual shapes based on multiple testing within a certain period of time: $(\Sigma Sh_1)/(\Sigma Sh_1+\Sigma Sh_2+\Sigma F)$ and $(\Sigma Sh_1+\Sigma Sh_2)/(\Sigma Sh_1+\Sigma Sh_2+\Sigma F)$ 2. Segment completion and celerity performance scores/measures:
(analysis based on best of two attempts [highest number of completed segments] for each shape, if applicable)
   a. Number of successfully completed segments (0 to [2a+b+c+d+e−6]) ($\Sigma Se$) per test
   b. Mean celerity ([C], segments/second) of successfully completed segments: $C=\Sigma Se/t$, where t would represent the time in seconds to complete the test (max 30 seconds)
   c. Segment completion score reflecting the number of successfully completed segments adjusted with weighting factors for different complexity levels for respective shapes ($\Sigma[Se*Wf]$)
   d. Speed-adjusted and weighted segment completion score ($\Sigma[Se*Wf]*30/t$), where t would represent the time in seconds to complete the test
   e. Shape-specific number of successfully completed segments for linear and square shapes ($\Sigma Se_{LS}$)
   f. Shape-specific number of successfully completed segments for circular and sinusoidal shapes ($\Sigma Se_{CS}$)
   g. Shape-specific number of successfully completed segments for spiral shape ($\Sigma Se_S$)
   h. Shape-specific mean linear celerity for successfully completed segments performed in linear and square shape testing: $C_L=\Sigma Se_{LS}/t$, where t would represent the cumulative epoch time in seconds elapsed from starting to finishing points of the corresponding successfully completed segments within these specific shapes
   i. Shape-specific mean circular celerity for successfully completed segments performed in circular and sinusoidal shape testing: $C_C=\Sigma Se_{CS}/t$, where t would represent the cumulative epoch time in seconds elapsed from starting to finishing points of the corresponding successfully completed segments within these specific shapes
   j. Shape-specific mean spiral celerity for successfully completed segments performed in the spiral shape testing: $C_S=\Sigma Se_S/t$, where t would represent the cumulative epoch time in seconds elapsed from starting to finishing points of the corresponding successfully completed segments within this specific shape 3. Drawing precision performance scores/measures:
(analysis based on best of two attempts [highest number of completed segments] for each shape, if applicable)
   a. Deviation (Dev) calculated as the sum of overall area under the curve (AUC) measures of integrated surface deviations between the drawn trajectory and the target drawing path from starting to ending checkpoints that were reached for each specific shape divided by the total cumulative length of the corresponding target path within these shapes (from starting to ending checkpoints that were reached)
   b. Linear deviation ($Dev_L$) calculated as Dev in 3(a) but specifically from the linear and square shape testing results
   c. Circular deviation ($Dev_L$) calculated as Dev in 3(a) but specifically from the circular and sinusoidal shape testing results
   d. Spiral deviation ($Dev_S$) calculated as Dev in 3(a) but specifically from the spiral shape testing results
   e. Shape-specific deviation ($Dev_{1-6}$) calculated as Dev in 3(a) but from each of the 6 distinct shape testing results separately, only applicable for those shapes where at least 3 segments were successfully completed within the best attempt
   f. Continuous variable analysis of any other methods of calculating shape-specific or shape-agnostic overall deviation from the target trajectory The aim of the Squeeze a Shape test is to assess fine distal motor manipulation (gripping and grasping) and control by evaluating accuracy of pinch closed finger movement. The test is considered to cover the following aspects of impaired hand motor function: impaired gripping/grasping function, muscle weakness, and impaired hand-eye coordination. The patients are instructed to hold the mobile device in the untested hand and by touching the screen with two fingers from the same hand (thumb+second or thumb+third finger preferred) to squeeze/pinch as many round shapes (i.e., tomatoes) as they can during 30 seconds. Impaired fine motor manipulation will affect the performance. Test will be alternately performed with right and left hand. User will be instructed on daily alternation.

Typical Squeeze a Shape test performance parameters of interest:
1. Number of squeezed shapes
   a. Total number of tomato shapes squeezed in 30 seconds ($\Sigma Sh$)
   b. Total number of tomatoes squeezed at first attempt ($\Sigma Sh_1$) in 30 seconds (a first attempt is detected as the first double contact on screen following a successful squeezing if not the very first attempt of the test)
2. Pinching precision measures:
   a. Pinching success rate ($P_{SR}$) defined as $\Sigma Sh$ divided by the total number of pinching ($\Sigma P$) attempts (measured as the total number of separately detected double finger contacts on screen) within the total duration of the test
   b. Double touching asynchrony (DTA) measured as the lag time between first and second fingers touch the screen for all double contacts detected
   c. Pinching target precision ($P_{TP}$) measured as the distance from the midpoint between the starting touch points of the two fingers at double contact to the center of the tomato shape, for all double contacts detected d. Pinching finger movement asymmetry ($P_{FMA}$) measured as the ratio between respective distances slid by the two fingers (shortest/longest) from the double contact starting points until reaching pinch gap, for all double contacts successfully pinching e. Pinching finger velocity ($P_{FV}$) measured as the speed (mm/sec) of each one and/or both fingers sliding on the screen from time of double contact until reaching pinch gap, for all double contacts successfully pinching f. Pinching finger asynchrony ($P_{FA}$) measured as the ratio between velocities of respective individual fingers sliding on the screen (slowest/fastest) from the time of double contact until reaching pinch gap, for all double contacts successfully pinching g. Continuous variable analysis of 2(a) to 2(f) over time as well as their analysis by epochs of variable duration (5-15 seconds)

h. Continuous variable analysis of integrated measures of deviation from target drawn trajectory for all tested shapes (in particular the spiral and square)

(5) A computer-implemented test evaluating emotional status and well-being, in particular, the Mood Scale Question (MSQ).

In an embodiment, the mobile device is adapted for performing or acquiring data from a Mood Scale Question (MSQ) Questionnaire. Depression in its various forms is a common symptom of MS patients and if left untreated, it reduces quality of life, makes other symptoms—including fatigue, pain, cognitive changes—feel worse, and may be life-threatening (National MS Society). Therefore in order to assess patients' perceived overall state, they will be asked how they feel through a 5-item questionnaire on the mobile device. The questionnaire is typically performed daily.

Typical MSQ performance parameters of interest:
1. Proportion of days with excellent mood in the last week, month, and year.
2. Proportion of days with ≥good mood in the last week, month, and year.
3. Proportion of days with ≥decent mood in the last week, month, and year.
4. Proportion of days with horrible mood in the last week, month, and year.
5. Frequency distribution of response type by time of the day between 6-8 am, 8-10 a.m., 10 a.m.-12 p.m., 12-2 p.m., 2-4 p.m., 4-6 p.m., 6-8 p.m., 8 p.m.-12 a.m., 12-6 a.m. during the last month, and during the last year.

(6) A computer-implemented test evaluating quality of life, in particular, the 29-Item Multiple Sclerosis Impact Scale (MSIS29).

In one embodiment, the mobile device is adapted for performing or acquiring data from the Multiple Sclerosis Impact Scale (MSIS)-29 test. To assess the impact of MS on the daily life of subjects, they will be asked to complete MSIS-29 (Hobart 2001, Brain 124: 962-73) biweekly on the mobile device, which is a 29-item questionnaire designed to measure the physical (items 1-20) and psychological (items 21-29) impact of MS from the patient's perspective (Hobart 2001, loc. cit.). We will use the second version of MSIS-29 (MSIS-29 v.2), which has four-point response categories for each item: "not at all," "a little," "moderately," and "extremely." MSIS-29 scores range from 29 to 116. Scores on the physical impact scale can range from 20 to 80 and on the psychological impact scale from 9 to 36, with lower scores indicating little impact of MS and higher scores indicating greater impact. Questions 4 and 5, as well as questions 2, 6, and 15 of MSIS-29 v.2 related to ambulation/lower limb and hand/arm/upper limb physical functions, respectively will also be subject to separate cluster analysis. The test is performed, typically, bi-weekly.

Typical MSIS-29 (v2) performance parameters of interest:
1. MSIS-29 score (29-116)
2. MSIS-29 Physical Impact Score (20-80)
3. MSIS-29 Psychological Impact Score (9-36)
4. MSIS-29 ambulation/lower limb score (2-10)
5. MSIS-29 hand/arm/upper limb score (3-15)
6. Time-corrected/filtered MSIS-29 scores of 1-5 based on minimum time needed to comprehend a posed question and provide an answer
7. Certainty weighted MSIS-29 scores of 1-6 based on the number of changes of a given answer and the difference/variation between the answers provided
8. Fine finger motor skill function parameters captured during MSIS-29
    a. Continuous variable analysis of duration of touchscreen contacts (Tts)
    b. Continuous variable analysis of deviation between touchscreen contacts (Dts) and center of closest target digit key
    c. Number of mistyped touchscreen contacts (Mts) (sum of contacts not triggering key hit or triggering key hit but associated with secondary sliding on screen), while typing responses.
9. Ratio of 8a, 8b, and 8c variables during versus corresponding variables of eSDMT (transformation/normalization of 8c to represent the projected number of Mts if MSIS-29 per 90 seconds)

(7) A computer-implemented test tracking emerging new or worsening disease symptoms, in particular, the Multiple Sclerosis Symptom Tracker (MSST).

In yet another embodiment, the mobile device is adapted for performing or acquiring data from the Multiple Sclerosis Symptom Tracker (MSST). As the patient's perception of relapse occurrence and symptom variations may differ from clinically relevant symptom aggravation considered as a relapse, simple questions geared towards detecting new/worsening symptoms will be asked directly to the patients bi-weekly on the smartphone and synchronised with the MSIS-29 questionnaire. The patient has, in addition, the possibility to report symptoms and their respective calendar date of onset at any time. The MSST may, typically, be performed bi-weekly or on demand.

Typical MSST performance parameters of interest:
1. Number of reported episodes of "new or significantly worsening symptoms during the last two weeks" within the last month, and year (as per symptom onset date).
2. Proportion of total reported episodes of "new or significantly worsening symptoms during the last two weeks" that were considered to be "relapse(s)" vs. "not a relapse" vs. "unsure" within the last year.

(8) A computer-implemented passive monitoring of all or a predetermined subset of activities of a subject performed during a certain time window.

In yet another embodiment, the mobile device is adapted for performing or acquiring data from passive monitoring of all or a subset of activities In particular, the passive monitoring shall encompass monitoring one or more activities performed during a predefined window, such as one or more days or one or more weeks, selected from the group consisting of: measurements of gait, the amount of movement in daily routines in general, the types of movement in daily routines, general mobility in daily living and changes in moving behavior.

Typical passive monitoring performance parameters of interest:
a. frequency and/or velocity of walking;
b. amount, ability and/or velocity to stand up/sit down, stand still and balance;
c. number of visited locations as an indicator of general mobility; and
d. types of locations visited as an indicator of moving behavior.

It will be understood that the mobile device to be applied in accordance with the present disclosure may be adapted to perform one or more of the aforementioned activity tests. In particular, it may be adapted to perform one, two, three, four, five, six or all seven of these tests. Typically, combinations of tests may be implemented on the mobile device. Said combinations, more typically, comprise any one or all of test numbers (5) to (7) and any one or all of test numbers (1) to (4) or (8). More particular, at least a test for fine motoric assessment as specified as test number (4) shall be implemented on the mobile device and, most typical, the Draw a Shape test and/or the Squeeze a Shape test.

Moreover, the mobile device may be adapted to perform further MS tests such as computer-implemented versions of other cognitive tests and/or the visual contrast acuity tests (such as low contrast letter acuity or Ishihara test; see, e.g., Bove 2015, loc. cit.).

Further data may be processed in the method of this disclosure as well. These further data are typically suitable for further strengthening the identification of progressing MS in a subject. Typically, such data may be parameters from biochemical biomarkers for MS or data from imaging methods such as cross-sectional and/or longitudinal Magnetic Resonance Imaging (MRI) measures of whole brain volume, brain parenchymal fraction, whole grey matter volume, cortical grey matter volume, volume of specific cortical areas, deep grey matter volume, thalamic volume, corpus callosum surface or thickness, white matter volume, third ventricle volume, total brain T2-weighted hyperintense lesion volume, total cortical lesion volume, total brain T1-weighted hypointense lesion volume, total brain FLAIR (Fluid Attenuation Inversion Recovery) lesion volume, total new and/or enlarging T2 and FLAIR lesion number and volume, as assessed using automated algorithmic solution software, such as but not exclusively MSmetrix™, or NeuroQuant™.

The term "mobile device" as used herein refers to any portable device which comprises a sensor and data-recording equipment suitable for obtaining the dataset of activity measurements. Typically, the mobile device comprises a sensor for measuring the activity. This may also require a data processor and storage unit as well as a display for electronically simulating an activity test on the mobile device. Moreover, from the activity of the subject data shall be recorded and compiled to a dataset which is to be evaluated by the method of this disclosure either on the mobile device itself or on a second device. Depending on the specific setup envisaged, it may be necessary that the mobile device comprises data transmission equipment in order to transfer the acquired dataset from the mobile device to a further device. Particularly well suited as mobile devices according to the present disclosure are smartphones, portable multimedia devices or tablet computers. Alternatively, portable sensors with data recording and processing equipment may be used. Further, depending on the kind of activity test to be performed, the mobile device shall be adapted to display instructions for the subject regarding the activity to be carried out for the test. Particular envisaged activities to be carried out by the subject are described elsewhere herein and encompass the following tests: eSDMT, 2-Minute Walking Test (2MWT), 5 U-Turn Test (5UTT), Static balance test (SBT), Continuous Analysis of Gait (CAG), Draw a Shape, Squeeze a Shape, visual contrast acuity tests (such as low contrast letter acuity or Ishihara test), as well as other tests described in this specification.

Determining at least one performance parameter can be achieved either by deriving a desired measured value from the dataset as the performance parameter directly. Alternatively, the performance parameter may integrate one or more measured values from the dataset and, thus, may be derived from the dataset by mathematical operations. Typically, the performance parameter is derived from the dataset by an automated algorithm, e.g., by a computer program which automatically derives the performance parameter from the dataset of activity measurements when tangibly embedded on a data processing device feed by the said dataset.

The term "reference" as used herein refers to a discriminator which allows the identification of a subject with progressing MS. Such a discriminator may be a value for the performance parameter which is indicative for subjects with progressing MS.

Such a value may be derived from one or more performance parameters of subjects known to suffer from progressing MS. Typically, the average or median may be used as a discriminator in such a case. If the determined performance parameter from the subject is identical to the reference or above a threshold derived from the reference, the subject can be identified as suffering from progressing MS in such a case. If the determined performance parameter differs from the reference and, in particular, is below the said threshold, the subject shall be identified as not suffering from progressing MS Similarly, a value may be derived from one or more performance parameters of subjects known not to suffer from progressing MS. Typically, the average or median may be used as a discriminator in such a case. If the determined performance parameter from the subject is identical to the reference or below a threshold derived from the reference, the subject can be identified as not suffering from progressing MS in such a case. If the determined performance parameter differs from the reference and, in particular, is above the said threshold, the subject shall be identified as suffering from progressing MS.

As an alternative, the reference may be a previously determined performance parameter from a dataset of activity measurements which has been obtained from the same subject prior to the actual dataset. In such a case, a determined performance parameter determined from the actual dataset which differs with respect to the previously determined performance parameter shall be indicative for either an improvement or worsening depending on the previous status of the disease and the kind of activity represented by the performance parameter. The skilled person knows based on the kind of activity and previous performance parameter how the said parameter can be used as a reference.

Comparing the determined at least one performance parameter to a reference can be achieved by an automated comparison algorithm implemented on a data processing device such as a computer. The values of a determined performance parameter and a reference for said determined performance parameter are compared to each other as specified elsewhere herein in detail. As a result of the comparison, it can be assessed whether the determined performance parameter is identical, similar, or differs from or is in a certain relation to the reference (e.g., is larger or lower than the reference). Based on said assessment, the subject can be identified as suffering from progressing MS ("rule-in"), or not ("rule-out"). For the assessment, the kind of reference will be taken into account as described elsewhere in connection with suitable references according to this disclosure.

Moreover, by determining the degree of difference between a determined performance parameter and a reference, a quantitative assessment of progressing MS in a subject shall be possible. It is to be understood that an improvement, worsening or unchanged overall disease condition or of symptoms thereof can be determined by comparing an actually determined performance parameter to an earlier determined one used as a reference. Based on quatitative differences in the value of the said performance parameter the improvement, worsening or unchanged condition can be determined and, optionally, also quantified. If other references, such as references from subjects with progressing MS are used, it will be understood that the quantitative differences are meaningful if a certain disease stage can be allocated to the reference collective. Relative to this disease stage, worsening, improvement or unchanged disease condition can be determined in such a case and, optionally, also quantified.

The said diagnosis, i.e., the identification of the subject as being a subject suffering from progressing MS, or not, is indicated to the subject or other person, such as a medical practitioner. Typically, this is achieved by displaying the diagnosis on a display of the mobile device or the evaluation device. Alternatively, a recommendation for a therapy, such as a drug treatment, or for a certain life style, e.g., a certain nutritional diet or rehabilitation measures, is provided automatically to the subject or other person. To this end, the established diagnosis is compared to recommendations allocated to different diagnoses in a database. Once the established diagnosis matches one of the stored and allocated diagnoses, a suitable recommendation can be identified due to the allocation of the recommendation to the stored diagnosis matching the established diagnosis. Accordingly, it is, typically, envisaged that the recommendations and diagnoses are present in the form of a relational database. However, other arrangements which allow for the identification of suitable recommendations are also possible and known to the skilled artisan.

Moreover, the one or more performance parameter may also be stored on the mobile device or indicated to the subject, typically, in real time. The stored performance parameters may be assembled into a time course or similar evaluation measures. Such evaluated performance parameters may be provided to the subject as a feedback for activity capabilities investigated in accordance with the method of this disclosure. Typically, such a feedback can be provided in electronic format on a suitable display of the mobile device and can be linked to a recommendation for a therapy as specified above or rehabilitation measures.

Further, the evaluated performance parameters may also be provided to medical practitioners in doctor's offices or hospitals as well as to other health care providers, such as, developers of diagnostic tests or drug developers in the context of clinical trials, health insurance providers or other stakeholders of the public or private health care system.

Typically, the method of the present disclosure for identifying a subject suffering from progressing MS may be carried out as follows:

First, at least one performance parameter is determined from an existing dataset of activity measurements obtained from said subject using a mobile device. Said dataset may be transmitted from the mobile device to an evaluating device, such as a computer, or may be processed in the mobile device in order to derive the at least one performance parameter from the dataset.

Second, the determined at least one performance parameter is compared to a reference by, e.g., using a computer-implemented comparison algorithm carried out by the data processor of the mobile device or by the evaluating device, e.g., the computer. The result of the comparison is assessed with respect to the reference used in the comparison and based on the said assessment the subject will be identified as a subject suffering from progressing MS, or not.

Third, the said diagnosis, i.e., the identification of the subject as being a subject suffering from progressing MS, or not, is indicated to the subject or other person, such as a medical practitioner.

Alternatively, a recommendation for a therapy, such as a drug treatment, or for a certain life style, e.g., a certain nutritional diet, is provided automatically to the subject or other person. To this end, the established diagnosis is compared to recommendations allocated to different diagnoses in a database. Once the established diagnosis matches one of the stored and allocated diagnoses, a suitable recommendation can be identified due to the allocation of the recommendation to the stored diagnosis matching the established diagnosis. Typical recommendations involve therapy with an anti-CD20 antibody as described elsewhere herein.

Yet as an alternative or in addition, the at least one performance parameter underlying the diagnosis will be stored on the mobile device. Typically, it shall be evaluated together with other stored performance parameters by suitable evaluation tools, such as time course assembling algorithms, implemented on the mobile device which can assist with rehabilitation or therapy recommendations as specified elsewhere herein.

This disclosure, in light of the above, also specifically contemplates a method of identifying progressing multiple sclerosis (MS) in a subject comprising the steps of:
 a) obtaining from said subject using a mobile device a dataset of activity measurements during predetermined activity performed by the subject;
 b) determining at least one performance parameter determined from a dataset of activity measurements obtained from said subject using a mobile device;
 c) comparing the determined at least one performance parameter to a reference; and
 d) identifying progressing MS in a subject based on the comparison carried out in step (b).

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once. Further, it should be understood that all terms used throughout this disclosure and claims, regardless of whether said terms are preceded by the phrases "one or more," "at least one," or the like, should not receive a singular interpretation unless it is made explicit herein. That is, all terms used in this disclosure and claims should generally be interpreted to mean "one or more" or "at least one."

Further, as used in the following, the terms "particularly," "more particularly," "specifically," "more specifically," "typically," and "more typically" or similar terms are used in conjunction with additional/alternative features, without restricting alternative possibilities. Thus, features introduced by these terms are additional/alternative features and are not intended to restrict the scope of the claims in any way. The invention may, as the skilled person will recognize, be performed by using alternative features. Similarly, features introduced by "in an embodiment of the invention" or similar expressions are intended to be additional/alternative features, without any restriction regarding alternative embodiments of the invention, without any restrictions regarding the scope of the invention and without any restriction regarding the possibility of combining the features introduced in such way with other additional/alternative or non-additional/alternative features of the invention.

Advantageously, it has been found in the studies underlying the present disclosure that performance parameters obtained from datasets measured during certain activities of MS patients can be used as digital biomarkers for identifying those patients which suffer from progressing MS. The said datasets can be acquired from the MS patients in a convenient manner by using mobile devices such as the omnipresent smart phones, portable multimedia devices or tablet computers. The datasets thereby acquired can be subsequently evaluated by the method of the invention for the performance parameter suitable as digital biomarker. Said evaluation can be carried out on the same mobile device or it can be carried out on a separate remote device. Moreover, by using such mobile devices, recommendations on life style or therapy can be provided to the patients directly, i.e., without the consultation of a medical practitioner in a doctor's office or hospital ambulance. Thanks to the present invention, the life conditions of MS patients, in particular, of those with progressing MS, can be adjusted more precisely to the actual disease status due to the use of actual determined performance parameters by the method of this disclosure. Thereby, drug treatments can be selected that are more efficient or dosage regimens can be adapted to the current status of the patient. It is to be understood that the method of the invention is, typically, a data evaluation method which requires an existing dataset of activity measurements from a subject. Within this dataset, the method determines at least one performance parameter which can be used for identifying progressing MS, i.e., which can be used as a digital biomarker for progressing MS.

Accordingly, the method of the present disclosure may be used for:
   assessing the disease condition;
   monitoring patients, in particular, in a real life, daily situation and on large scale;
   supporting patients with life style and/or therapy recommendations;
   investigating drug efficacy, e.g., also during clinical trials;
   facilitating and/or aiding therapeutic decision making;
   supporting hospital management;
   supporting rehabilitation measure management;
   improving the disease condition as a rehabilitation instrument stimulating higher density cognitive, motoric and walking activity
   supporting health insurance assessments and management; and/or
   supporting decisions in public health management.

The explanations and definitions for the terms made above apply mutatis mutandis to the embodiments described herein below.

In the following, particular embodiments of the method of the present disclosure are described:

In one embodiment of the method of the invention, said progressing multiple sclerosis is relapsing-remitting MS with clinical disease activity, is relapsing-remitting MS with disability progression, is secondary progressive MS, is secondary progressive MS with disability progression, is primary progressive MS, or is primary progressive MS with disability progression.

In yet another embodiment of the method of the present disclosure, said at least one performance parameter is a parameter indicative for the subject's motoric and/or fine motoric capabilities and function, walking, color vision, attention, dexterity and/or cognitive capabilities, quality of life, fatigue, mental state, mood, vision and/or cognition.

In another embodiment of the method of the invention, the said dataset of activity measurements comprises data from at least one test selected from the group consisting of: eSDMT, 2-Minute Walking Test (2MWT), 5 U-Turn Test (5UTT), Static balance test (SBT), Continuous Analysis of Gait (CAG), Draw a shape and Squeeze a shape, visual contrast acuity tests (such as low contrast letter acuity or Ishihara test), Mood Scale Question (MSQ), MSIS-29, and passive monitoring of all or a predetermined subset of activities of a subject performed during a certain time window.

In a further embodiment of the method of this disclosure, the said dataset of activity measurements comprises data from the eSDMT, 2-Minute Walking Test (2MWT), 5 U-Turn Test (5UTT), Static balance test (SBT), Continuous Analysis of Gait (CAG), Draw a shape, and Squeeze a shape.

In an embodiment of the method of the present disclosure, said mobile device has been adapted for carrying out on the subject one or more of the tests referred to above and, in particular, at least one test selected from the group consisting of: eSDMT, 2-Minute Walking Test (2MWT), 5 U-Turn Test (5UTT), Static balance test (SBT), Continuous Analysis of Gait (CAG), Draw a shape and Squeeze a shape, visual contrast acuity tests (such as low contrast letter acuity or Ishihara test), Mood Scale Question (MSQ), MSIS-29, and passive monitoring of all or a predetermined subset of activities of a subject performed during a certain time window.

In a further embodiment of the method of the present disclosure, said mobile device is comprised in a smartphone, smartwatch, wearable sensor, portable multimedia device or tablet computer.

In another embodiment of the method of the present disclosure, said reference is at least one performance parameter derived from a dataset of activity measurements obtained from the said subject at a time point prior to the time point when the dataset of activity measurements referred to in step a) has been obtained from the subject. Typically, in said embodiment a worsening between the determined at least one performance parameter and the reference is indicative of a subject with progressing MS.

In yet another embodiment of the method of the present disclosure, said reference is at least one performance parameter derived from a dataset of activity measurements obtained from a subject or group of subjects known to suffer from progressing MS. Typically, in said embodiment a determined at least one performance parameter being essentially identical compared to the reference is indicative of a subject with progressing MS.

In yet another embodiment of the method of this disclosure, said reference is at least one performance parameter derived from a dataset of activity measurements obtained from a subject or group of subjects known not to suffer from progressing MS. Typically, in said embodiment a determined at least one performance parameter being worsened compared to the reference is indicative of a subject with progressing MS.

The present disclosure also contemplates a computer program, computer program product or computer readable storage medium having tangibly embedded said computer program, wherein the computer program comprises instructions when run on a data processing device or computer carry out the disclosed method as specified above. Specifically, the present disclosure further encompasses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer script, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, a computer program product having program code means, wherein the program code means can be stored or are stored on a storage medium, for performing the method according to one of the embodiments described in this description, if the program code means are executed on a computer or on a computer network, a data stream signal, typically encrypted, comprising a dataset of activity measurements obtained from the subject using a mobile device, and a data stream signal, typically encrypted, comprising the at least one performance parameter derived from the dataset of activity measurements obtained from the subject using a mobile device.

The present disclosure further relates to a method of determining at least one performance parameter from a dataset of activity measurements obtained from a subject using a mobile device comprising the steps of:
  a) deriving said at least one performance parameter from a dataset of activity measurements obtained from said subject using a mobile; and
  b) comparing the determined at least one performance parameter to a reference,
wherein, typically, said at least one performance parameter can aid the identifying progressing multiple sclerosis (MS) in a subject.

The present invention also encompasses a method of recommending an anti-CD20 antibody therapy against MS comprising the steps of the method described above and the further step of recommending the anti-CD20 antibody therapy if the subject suffers from progressing MS.

The term "anti-CD20 antibody" as used herein relates to monoclonal antibodies and derivatives thereof such as fully human, humanized, chimeric or single chain antibodies as well as polyclonal antisera which specifically recognize the CD20 surface molecule on so-called B cells under physiological conditions in the body. In particular, the drug Ocrelizumab is encompassed as an anti-CD20 antibody according to the present disclosure (see, e.g., Hutas 2008, Current opinion in investigational drugs 9 (11):1206-15). Ocrelizumab is useful as treatment in subjects suffering from progressing MS. Accordingly, an anti-CD20 antibody based therapy may be recommended if progressing MS is diagnosed in a subject. The anti-CD20 antibody according to the present disclosure shall typically result in B cell depletion. Suitable anti-CD20 antibodies according to the disclosure can be generated by the molecular biology techniques for generating monoclonal antibodies such as those described by Köhler 1975, Nature 256: 495-497. Techniques for making chimeric and, in particular, humanized antibodies are also well known in the art. Typically, a monoclonal anti-CD20 antibody to be applied as anti-CD20 antibody according to this disclosure is a chimeric, humanized or fully human antibody. Moreover, suitable anti-CD20 antibodies may also be obtained by developing already existing anti-CD20 monoclonal antibodies such as Rituximab further.

In an embodiment of the aforementioned method, said anti-CD20 antibody is Ocrelizumab.

The present disclosure also provides for a method of treating progressing MS in a subject suspected to suffer therefrom comprising the steps of any of the aforementioned methods and the further step of administering the anti-CD20 antibody as anti-CD20 antibody therapy to a subject which was identified to suffer from progressing MS and/or for which the therapy was recommended in a therapeutically effective amount.

The present disclosure also encompasses a method for determining efficacy of a therapy against progressing MS comprising the steps of the method, in particular, the steps of a) determining at least one performance parameter determined from a dataset of activity measurements obtained from said subject using a mobile device, and b) comparing the determined at least one performance parameter to a reference, whereby a subject with progressing MS will be identified or embodiments thereof specified elsewhere herein and the further step of determining a therapy response if improvement of progressing MS occurs in the subject upon therapy or determining a failure of response if worsening of progressing MS occurs in the subject upon therapy or if the progressing MS remains unchanged.

The term "improvement" as referred to in accordance with this disclosure relates to any improvement of the overall disease condition of progressing MS or of individual symptoms thereof. Likewise, a "worsening" means any worsening of the overall disease condition or individual symptoms thereof. Since progressing MS is associated typically with a worsening of the overall disease condition and symptoms thereof, the worsening referred to in connection with the aforementioned method is an unexpected or untypical worsening which goes beyond the normal course of progressing MS. Unchanged remaining progressing MS means that the overall disease condition and the symptoms accompanying it are within the normal course of progressing MS.

Moreover, the present disclosure pertains to a method of monitoring progressing MS in a subject comprising determining whether progressing MS improves, worsens or remains unchanged in a subject by carrying out the steps of the method, in particular, the steps of a) determining at least one performance parameter determined from a dataset of activity measurements obtained from said subject using a mobile device, and b) comparing the determined at least one performance parameter to a reference, whereby a subject with progressing MS will be identified or embodiments thereof specified elsewhere herein at least two times during a predefined monitoring period.

The term "predefined monitoring period" as used herein refers to a predefined time period in which at least two times activity measurements are carried out. Typically, such a period may range from days to weeks to months to years depending on the disease progression to be expected for the individual subject. Within the monitoring period, the activity measurements and performance parameters are determined at a first time point which is usually the start of the monitoring period and at least one further time point. However, it is also possible that there is more than one further time point for activity measurements and performance parameter determination. In any event, the performance parameter(s) determined from the activity measurements of the first time point are compared to the performance parameters of subsequent time points. Based on such a comparison, quantitative differences can be identified which will be used to determine a worsening, improvement or unchanged disease condition during the predefined monitoring period.

This disclosure relates to a mobile device comprising a processor, at least one sensor and a database as well as software which is tangibly embedded in said device and, when running on said device, carries out the method of the present disclosure.

The said mobile device is, thus, configured to be capable of acquiring the dataset and to determine the performance parameter therefrom. Moreover, it is configured to carry out the comparison to a reference and to establish the diagnosis, i.e., the identification of the subject as one suffering from progressing MS. Further details on how the mobile device can be designed for said purpose have been described elsewhere herein already in detail.

A system comprising a mobile device comprising at least one sensor and a remote device comprising a processor and a database as well as software which is tangibly embedded to said device and, when running on said device, carries out any of the disclosed methods, wherein said mobile device and said remote device are operatively linked to each other.

Under "operatively linked to each other" it is to be understood that the devices are connect as to allow data transfer from one device to the other device. Typically, it is envisaged that at least the mobile device which acquires data from the subject is connected to the remote device carrying out the steps of the methods of the disclosure such that the acquired data can be transmitted for processing to the remote device. However, the remote device may also transmit data to the mobile device such as signals controlling or supervising its proper function. The connection between the mobile device and the remote device may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Further details may be found elsewhere in this specification. For data acquisition, the mobile device may comprise a user interface such as screen or other equipment for data acquisition. Typically, the activity measurements can be performed on a screen comprised by a mobile device, wherein it will be understood that the said screen may have different sizes including, e.g., a 5.1 inch screen.

Moreover, it will be understood that the use of the mobile device or the system according to the present disclosure for identifying a subject suffering from progressing multiple sclerosis (MS) is contemplated.

The present disclosure also contemplates the use of the mobile device or the system for monitoring patients, in particular, in a real life, daily situation and on large scale.

Encompassed by the present invention is furthermore the use of the mobile device or the system according to the present disclosure for supporting patients with life style and/or therapy recommendations.

Yet, it will be understood that the present disclosure contemplates the use of the mobile device or the system for investigating drug efficacy, e.g., also during clinical trials.

Further, this disclosure contemplates the use of the mobile device or the system for facilitating and/or aiding therapeutic decision making.

Furthermore, the present invention provides for the use of the mobile device or the system according to the present disclosure for improving the disease condition as a rehabilitation instrument, and for supporting hospital management, rehabilitation measure management, health insurance assessments and management and/or supporting decisions in public health management.

Further particular embodiments are also listed as follows:

EMBODIMENT 1

A method of identifying progressing multiple sclerosis (MS) in a subject comprising the steps of:
  a) determining at least one performance parameter determined from a dataset of activity measurements obtained from said subject using a mobile device; and
  b) comparing the determined at least one performance parameter to a reference, whereby a subject with progressing MS will be identified.

EMBODIMENT 2

The method of embodiment 1, wherein said progressing multiple sclerosis is relapsing-remitting MS with clinical disease activity, is relapsing-remitting MS with disability progression, is secondary progressive MS, is secondary progressive MS with disability progression, is primary progressive MS, or is primary progressive MS with disability progression.

EMBODIMENT 3

The method of embodiment 1 or 2, wherein the said at least one performance parameter is a parameter indicative for the subject's motoric and/or fine motoric capabilities and function, walking, color vision, attention, dexterity and/or cognitive capabilities, quality of life, fatigue, mental state, mood, vision and/or cognition.

EMBODIMENT 4

The method of any one of embodiments 1 to 3, wherein the said dataset of activity measurements comprises data from at least one test selected from the group consisting of: 2-Minute Walking Test (2MWT), 5 U-Turn Test (5UTT), Static Balance test (SBT), eSDMT, CAG test, MSST test, Draw a Shape test, Squeeze a Shape test, Mood Scale Question test, MSIS-29, visual contrast acuity tests (such as low contrast letter acuity or Ishihara test), and passive monitoring of all or a predetermined subset of activities of a subject performed during a certain time window.

EMBODIMENT 5

The method of embodiment 4, wherein the said dataset of activity measurements comprises data from the 2-Minute Walking Test (2MWT), 5 U-Turn Test (5UTT), Static balance test (SBT), eSDMT, CAG test, Draw a Shape test, and Squeeze a Shape test.

EMBODIMENT 6

The method of any one of embodiments 1 to 5, wherein said mobile device has been adapted for carrying out on the subject one or more of the tests referred to in claim 4.

EMBODIMENT 7

The method of embodiment 6, wherein said mobile device is comprised in a smartphone, smartwatch, wearable sensor, portable multimedia device or tablet computer.

EMBODIMENT 8

The method of any one of embodiments 1 to 7, wherein said reference is at least one performance parameter derived from a dataset of activity measurements obtained from the said subject at a time point prior to the time point when the dataset of activity measurements referred to in step a) has been obtained from the subject.

EMBODIMENT 9

The method of embodiment 8, wherein a worsening between the determined at least one performance parameter and the reference is indicative for a subject with progressing MS.

EMBODIMENT 10

The method of any one of embodiments 1 to 7, wherein said reference is at least one performance parameter derived from a dataset of activity measurements obtained from a subject or group of subjects known to suffer from progressing MS.

EMBODIMENT 11

The method of embodiment 10, wherein a determined at least one performance parameter being essentially identical compared to the reference is indicative for a subject with progressing MS.

EMBODIMENT 12

The method of any one of embodiments 1 to 7, wherein said reference is at least one performance parameter derived from a dataset of activity measurements obtained from a subject or group of subjects known not to suffer from progressing MS.

EMBODIMENT 13

The method of embodiment 12, wherein a determined at least one performance parameter being worsened compared to the reference is indicative for a subject with progressing MS.

EMBODIMENT 14

A method of recommending an anti-CD20 antibody therapy against MS comprising the steps of the method of any one of embodiments 1 to 13 and the further step of recommending the anti-CD20 antibody therapy if the subject suffers from progressing MS.

EMBODIMENT 15

The method of embodiment 14, wherein said anti-CD20 antibody is Ocrelizumab.

EMBODIMENT 16

A method for determining efficacy of a therapy against progressing MS comprising the steps of the method of any one of embodiments 1 to 13 and the further step of determining a therapy response if improvement of progressing MS occurs in the subject upon therapy or determining a failure of response if worsening of progressing MS occurs in the subject upon therapy or if the progressing MS remains unchanged.

EMBODIMENT 17

A method of monitoring progressing MS in a subject comprising determining whether progressing MS improves, worsens or remains unchanged in a subject by carrying out the steps of the method of any one of embodiments 1 to 13 at least two times during a predefined monitoring period.

EMBODIMENT 18

A mobile device comprising a processor, at least one sensor and a database as well as software which is tangibly embedded to said device and, when running on said device, carries out the method of any one of embodiments 1 to 17.

EMBODIMENT 19

A system comprising a mobile device comprising at least one sensor and a remote device comprising a processor and a database as well as software which is tangibly embedded to said device and, when running on said device, carries out the method of any one of embodiments 1 to 17, wherein said mobile device and said remote device are operatively linked to each other.

EMBODIMENT 20

A mobile device according to embodiment 18 or the system of embodiment 19 for use in identifying a subject suffering from progressing multiple sclerosis (MS).

All references cited throughout this specification are herewith incorporated by reference with respect to their entire disclosure content and with respect to the specific disclosure contents mentioned in the specification.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1A) Instructions are given to the patient on the screen of the smartphone; FIG. 1B) user interface for testing matching digits; FIG. 1C) user interface for testing matching symbols.

FIGS. 2A and 2B show a smartphone adapted for performing a computer-implemented SBT. FIG. 2A) Instructions are given to the patient on the screen of the smartphone; FIG. 2B) user interface for showing the time until completion of the activity.

FIG. 3A) Possible shapes to be drawn by the patient; FIG. 3B) Instructions are given to the patient on the screen of the smartphone; FIGS. 3C, 3D and 3E) user interface for testing drawing different shapes.

FIG. 4A) Instructions are given to the patient on the screen of the smartphone; FIGS. 4B, 4C and 4D) user interface showing the different stages of a squeezing the shape activity.

FIG. 5A shows the distribution of number of total responses. The accuracy rate is depicted in FIG. 5B.

FIGS. 6A, 6B, 6C, 6D, 6E and 6F show the time elapsed between subsequent responses (R) and subsequent correct responses (CR) in eSDMT tests. FIGS. 6A, 6C and 6E show the elapsed time between subsequent responses (R). FIGS. 6B, 6D and 6F show the elapsed time between subsequent correct responses (CR). The subject population is divided into three groups: FIG. 6A and FIG. 6B stem from subjects providing fewer than 32 (correct) responses (N=9); FIG. 6C and FIG. 6D stem from subjects providing between 32 and 39 (correct) responses (N=10); and FIG. 6E and FIG. 6F stem from subjects providing 40 or more (correct) responses (N=11) over the course of 90 seconds. The median of the elapsed time is plotted as line and the standard deviation is shown as shaded region.

FIGS. 7A, 7B, 7C and 7D show examples of responses (R) and correct responses (CR) profile of two subjects with quite distinct performances in eSDMT tests. FIG. 7A shows the cumulative responses (R) profile of two subjects over 90 seconds. FIG. 7C shows the elapsed time between subsequent responses (R) of two patients. FIG. 7B shows the cumulative correct responses (CR) profile of two patients over 90 seconds. FIG. 7D shows the elapsed time between subsequent correct responses (CR) of two patients.

FIG. 8A shows an overview of a subject performing the Squeeze a Shape test for 30 seconds. Circles 110 in FIG. 8B illustrate the touch events from the first finger and circles 112 show second finger touch. Circles 114 in FIG. 8B show whenever two contact points with the display were made at the same time. The vertical dotted lines show the start and end of a pinch attempt, respectively. Line 116 in FIG. 8C shows the distance between the two pinching fingers. FIG. 8D shows the speed of the first and second fingers. FIG. 8E depicts the location of the 9th tomato that is successfully pinched with the 13th pinch at first attempt. The circles show the finger movement trajectory on the touch screen. The box indicates that the pinch attempt was successful.

FIG. 9A depicts a subject with poor 9HPT. FIG. 9B shows the baseline subject chosen based on good SHPT performance.

FIG. 10B shows shape specific segmentation into sectors, and subsequent error per sector. FIG. 10C shows the range of error distances per subject, including median and IQR.

FIG. 11A depicts a subject with poor 9HPT. FIG. 11B shows the baseline subject chosen based on good SHPT performance.

FIG. 12B shows shape specific segmentation into sectors, and subsequent error per sector. FIG. 12C shows the range of error distances per subject, including median and IQR.

FIG. 13A shows visual tracing of specified shape. FIB. 13B shows velocity tracing of draw-a-shape task over time to complete. FIG. 13C shows acceleration tracing of Draw-a-Shape task over time to complete.

FIG. 17A shows turning speed measured with the 5UTT correlates with the T25FW (Spearman's correlation coefficient=−0.62, p<0.001; as well as the ambulation items of the MSIS-29 (items 4 and 5), Spearman's correlation coefficient=−0.57, p=0.001). FIG. 17B shows turning speed measured with the 5UTT correlates with the EDSS score (Spearman's correlation coefficient=−0.72, p<0.001; FIG. 17B).

DESCRIPTION AND EXAMPLES

The embodiments and examples described below are not intended to be exhaustive or to limit the invention to the precise forms disclosed in the following description. Rather, the embodiments are chosen and described so that others skilled in the art may appreciate and understand the principles and practices of this disclosure.

Example 1: A Computer-Implemented (Electronic) Symbol Digit Modalities Test (eSDMT)

Figure 1C:
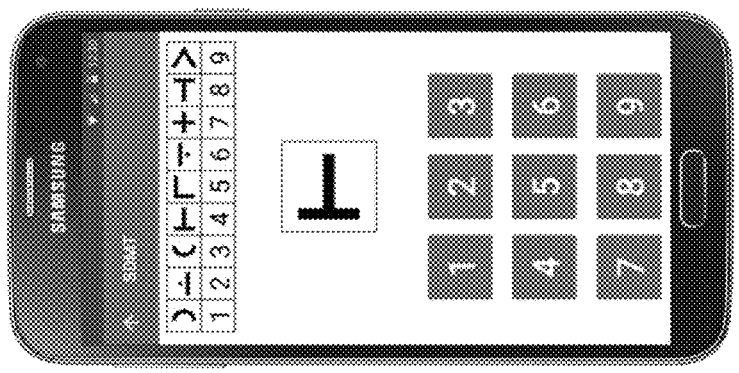
FIGS. 1A, 1B and 1C show a smartphone adapted for performing a computer-implemented eSDMT.
Figure 1B:
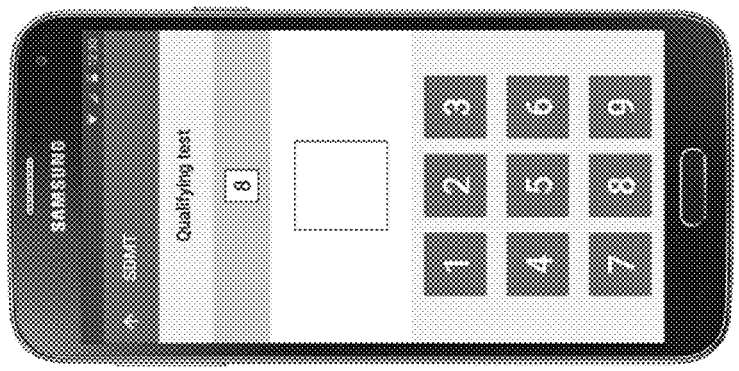
Figure 1A:
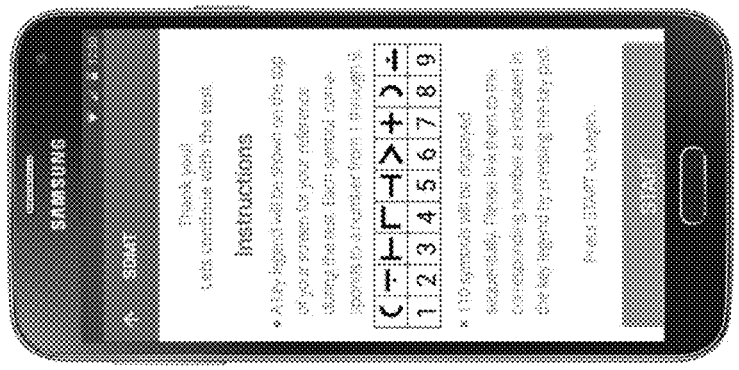
Figure 3A:
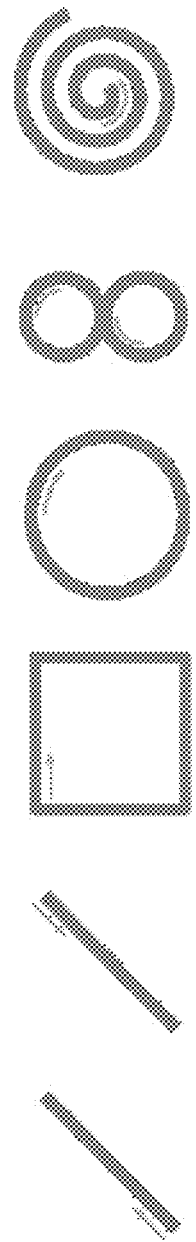
FIGS. 3A, 3B, 3C, 3D and 3E show a smartphone adapted for performing a computer implemented Draw a Shape test.
Figures 3B, 3C, 3D, 3E:
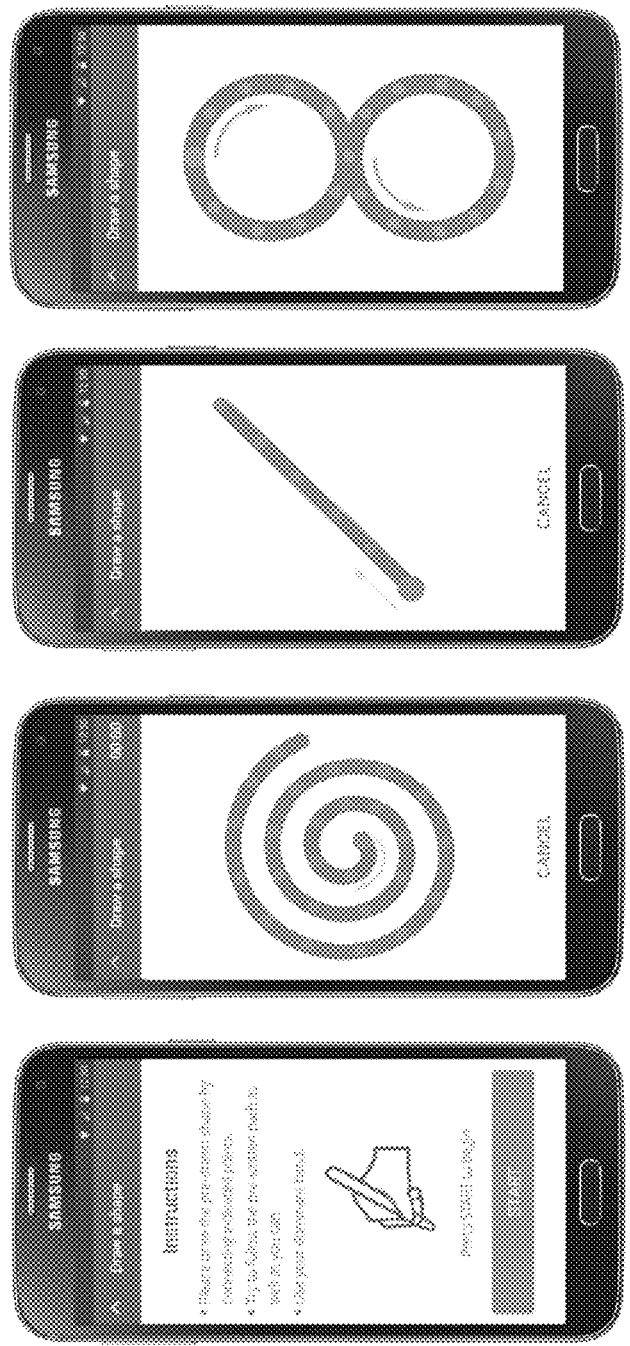
Figure 4D:
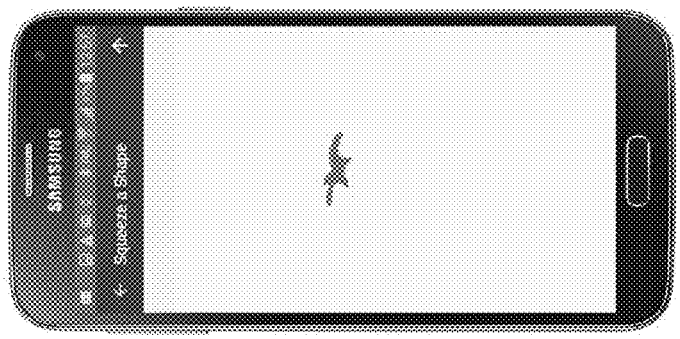
FIGS. 4A, 4B, 4C and 4D show a smartphone adapted for performing a computer implemented Squeeze a Shape test.
Figure 4C:
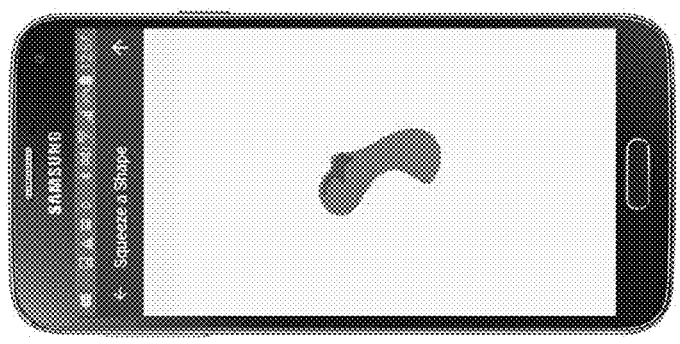
Figure 4B:
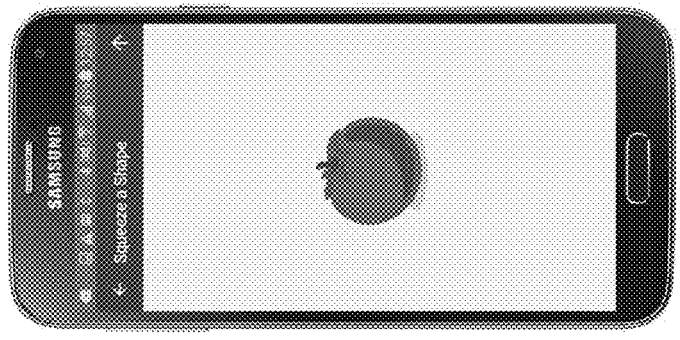
Figure 4A:
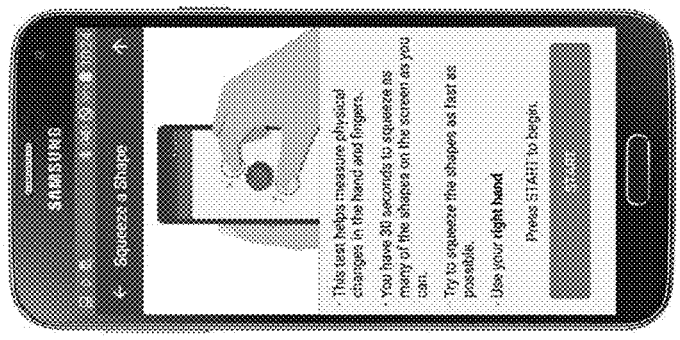
Figures 5A, 5B:
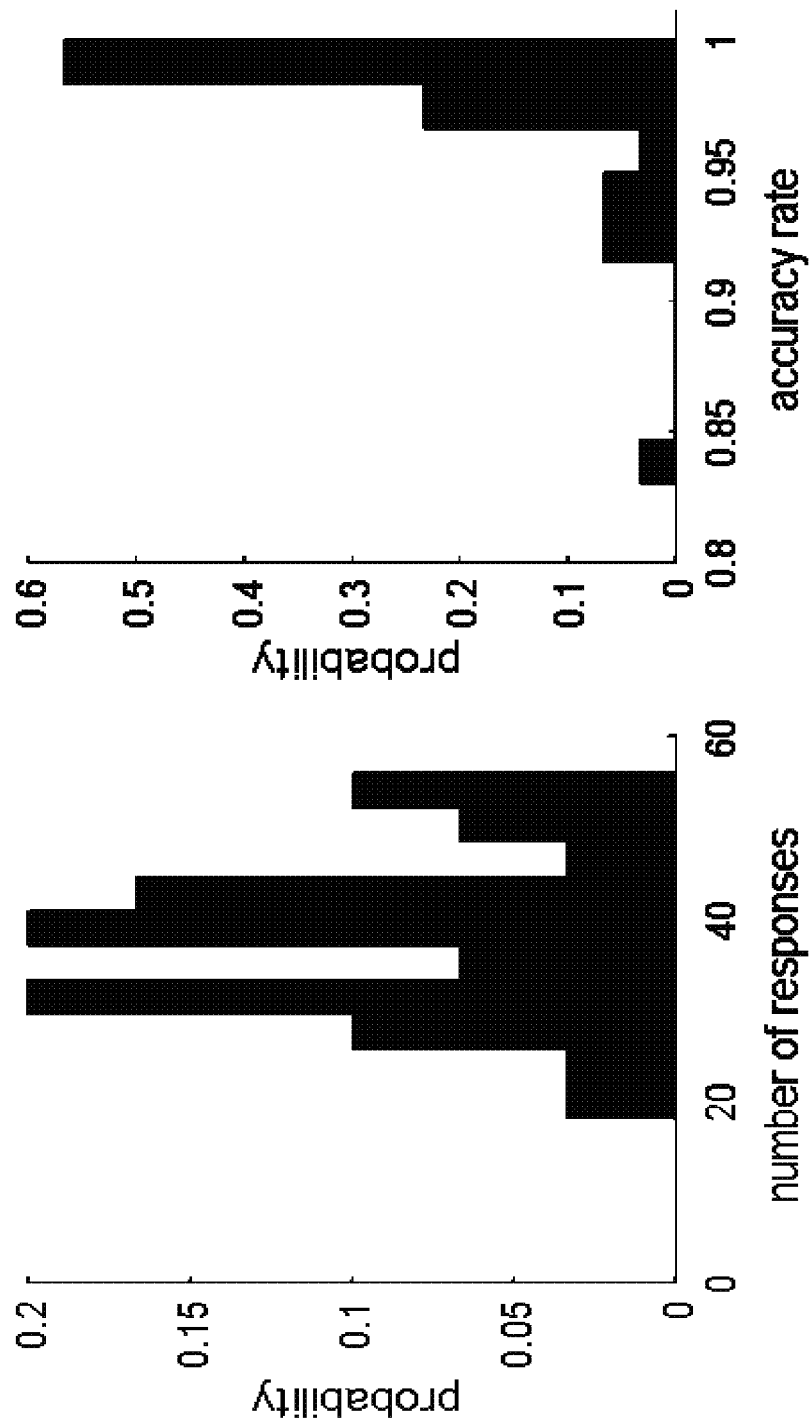
FIGS. 5A and 5B show an eSDMT test performance of 30 subjects.
Figure 8A:
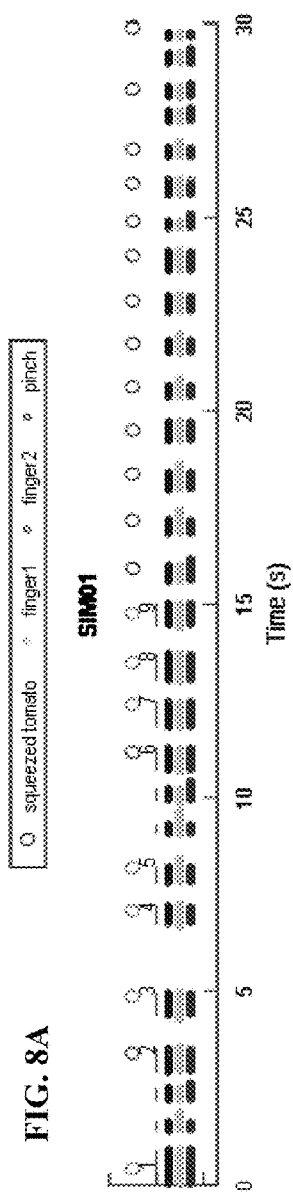
FIGS. 8A, 8B, 8C, 8D and 8E show an illustration of Squeeze a Shape test data.
Figure 8B:
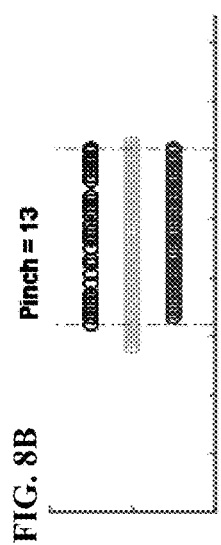
Figure 8C:
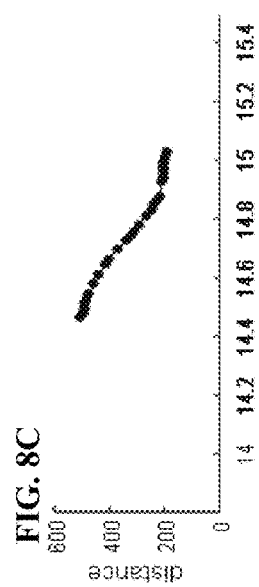
Figure 8D:
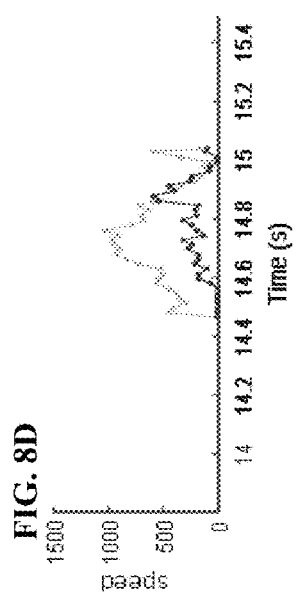
Figure 8E:

Smart phones with a 5.1 inch screen were programmed with suites for performing the eSDMT test. Test persons were asked to carry out the tests on the smart phone according to the instructions shown on the display. 30 subjects were investigated. The determined responses and accuracies are shown in FIG. 5.

The time elapsed between subsequent responses (R) and subsequent correct responses (CR) was also investigated in the implemented eSDMT tests. Results are shown in FIG. 6.

Furthermore, responses (R) and correct responses (CR) profiles were determined. Examples of responses (R) and correct responses (CR) profile of two subjects with quite distinct performances in eSDMT tests are shown in FIG. 7.

Example 2: A Computer-Implemented Test Evaluating Fine Motoric Capabilities (Fine Motoric Assessments), in Particular, Hand Motor Functions and, in Particular, the Touchscreen-Based "Draw a Shape" and "Squeeze a Shape" Tests Smart phones with a 5.1 inch screen were programmed with suites for performing the "Draw a Shape" and "Squeeze a Shape" tests. Test persons were asked to carry out the tests on the smart phone according to the instructions shown on the display.

Figure 9A:
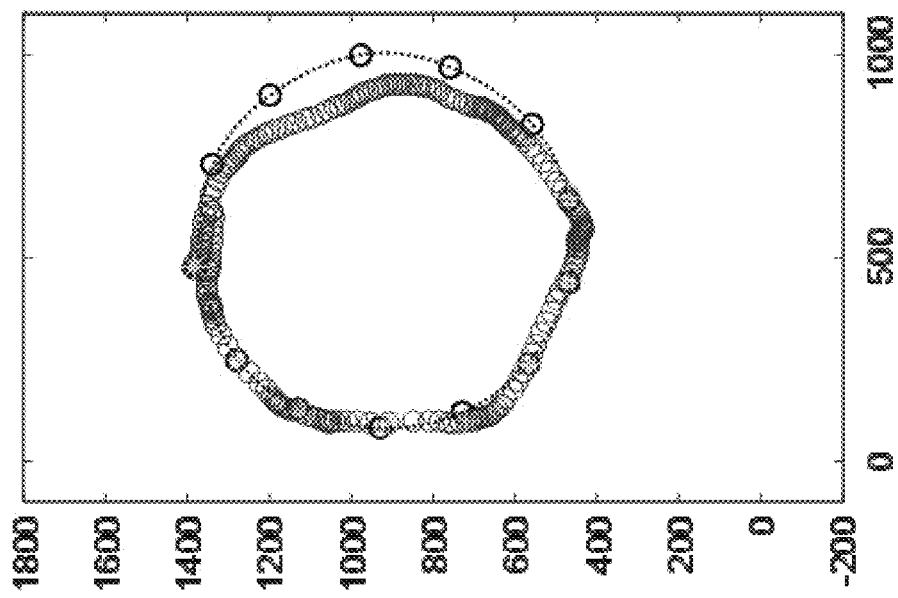
FIGS. 9A and 9B show examples of touch traces for circle shape from two subjects. Circles 120 along the dashed line indicate waypoints that subjects have to pass through. Circles 122 are the trace points. Each crosshair 118 represents the closest trace point 122 to each waypoint 120.
Figure 9B:
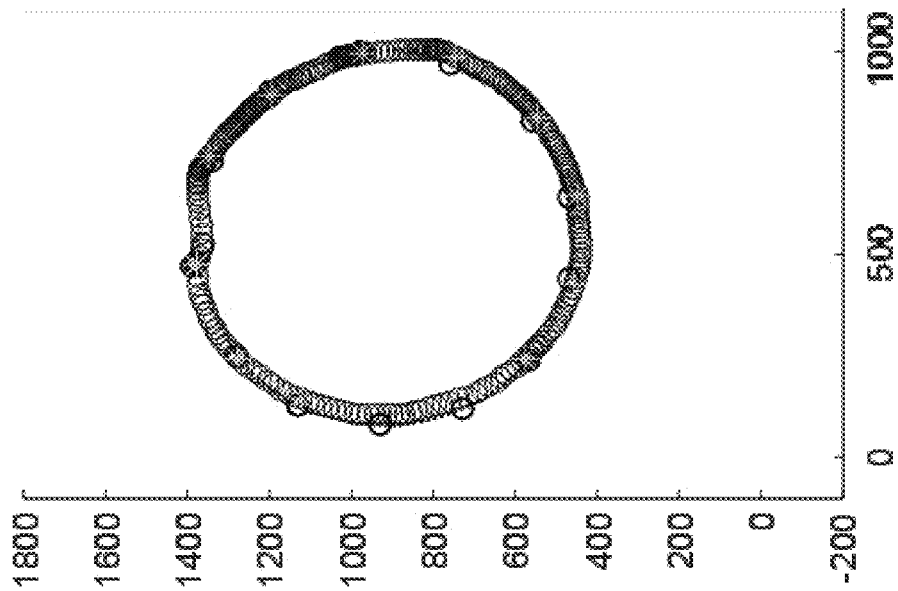
Figure 11B:
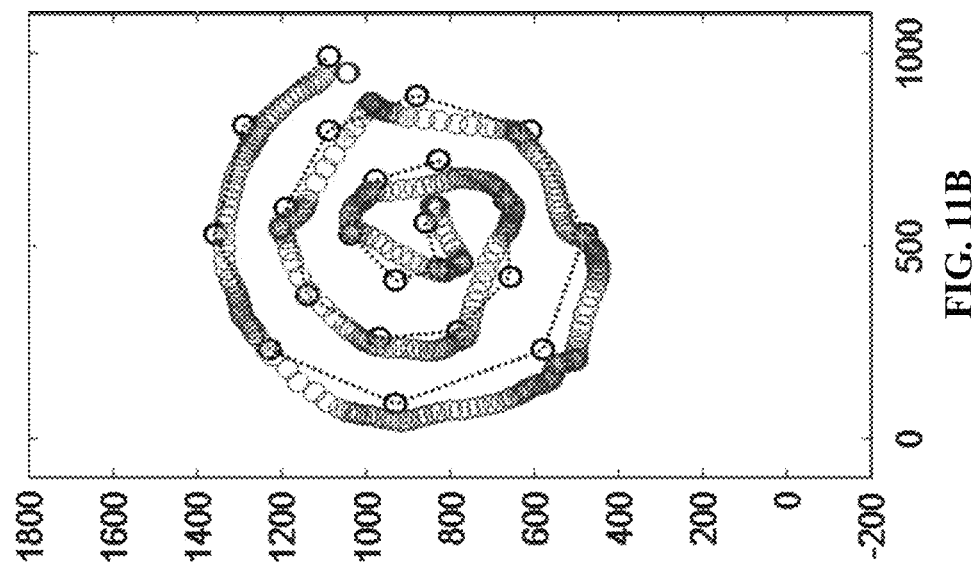
FIGS. 11A and 11B show examples of touch traces for spiral shape from two subjects. Circles 120 along the dashed line indicate waypoints that subjects have to pass through. Circles 122 are the trace points. Each crosshair 118 represents the closest trace point 122 to each waypoint 120.
Figure 11A:
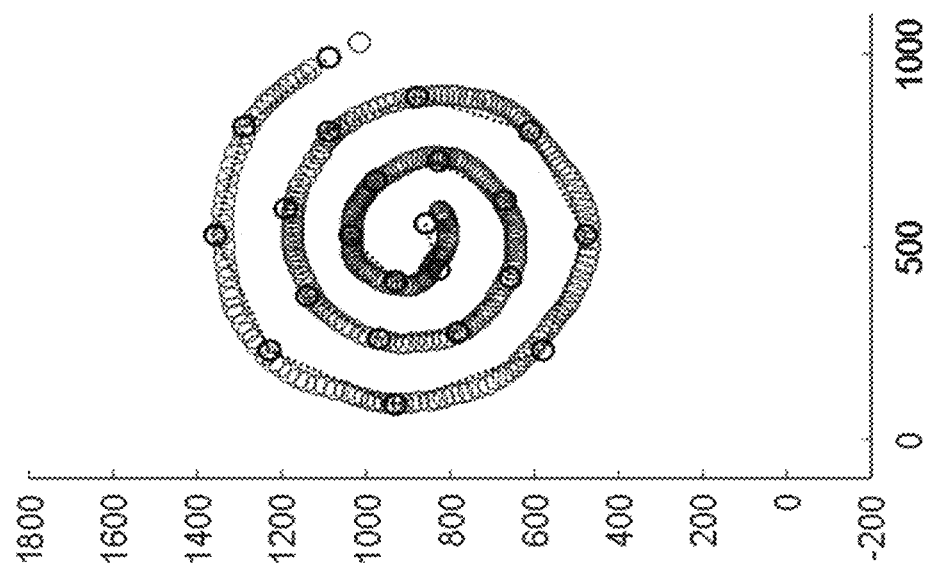

In the squeeze a shape set up, touch events from first and second fingers were determined and distances were calculated as well as the speed of the squeezing event (FIG. 8). In the draw a shape set up, touch traces for the circle shapes were determined. Results are depicted in FIG. 9 or 11.

Figure 10A:
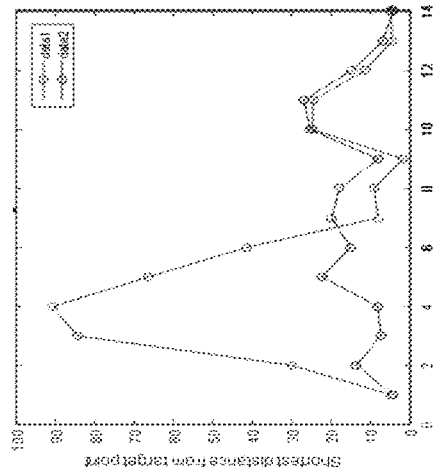
FIGS. 10A, 10B and 10C show tracing performance. Error distances per each waypoint of circle shape are shown in FIG. 10A.
Figure 10B:
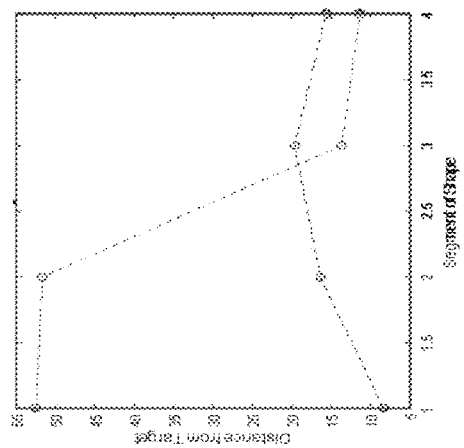
Figure 10C:
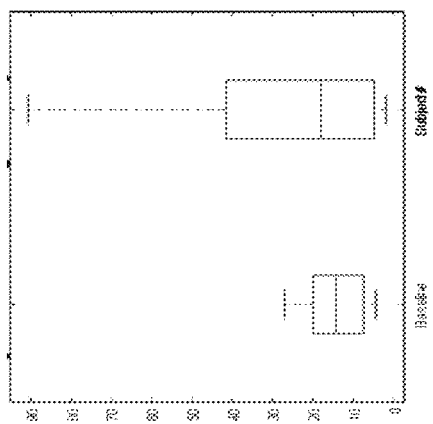
Figure 12C:
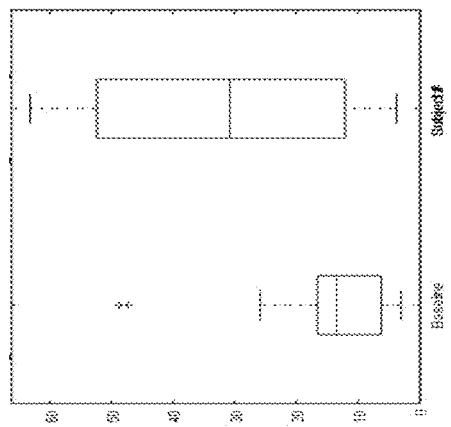
FIGS. 12A, 12B and 12C show the tracing performance for examples shown in FIGS. 11A and 11B. Error distances per each waypoint of spiral shape are shown in FIG. 12A.
Figure 12B:
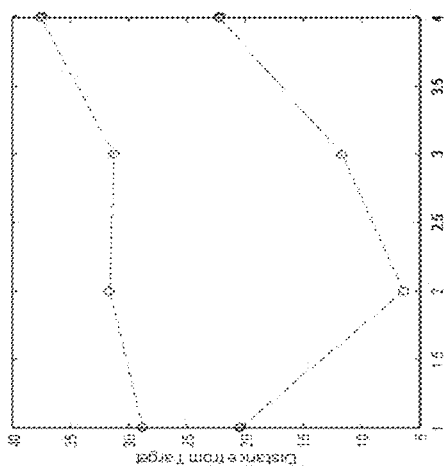
Figure 12A:
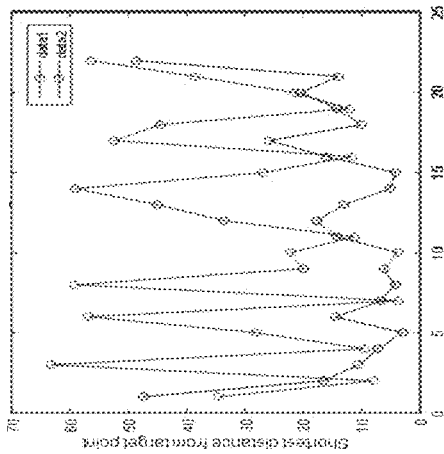

The overall calculated tracing performances are shown in FIGS. 10 and 12, respectively, and detailed data are summarized in Table 1 or 2, below.

TABLE 1

Circle assessment read-out performance statistics. The table lists performance measures of the two traces depicted in FIG. 9.

|  | Number of Hits | Accuracy | Time to Complete Shape [s] | Total Error | Mean Error | Std. Error |
| --- | --- | --- | --- | --- | --- | --- |
| Baseline subject | 12 | 85.71% | 3.31 sec | 195.34 | 13.95 | 7.69 |
| Poor performing subject | 9 | 64.28% | 3.52 sec | 407.25 | 29.09 | 30.56 |

TABLE 2

Spiral assessment read-out performance statistics. The table lists performance measures of the two traces depicted in FIG. 11.

|  | Number of Hits | Accuracy | Time to Complete Shape [s] | Total Error | Mean Error | Std. Error |
| --- | --- | --- | --- | --- | --- | --- |
| Baseline subject | 22 | 100% | 5.77 sec | 323.09 | 14.68 | 12.36 |
| Poor performing subject | 10 | 71.4% | 7.01 sec | 558.025 | 25.37 | 15.19 |

Figure 13B:
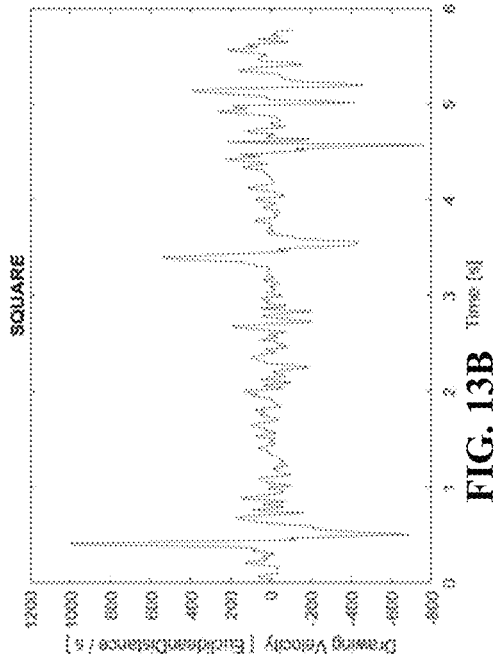
FIGS. 13A, 13B, and 13C show the collective spatial and temporal characteristics of a subjects drawing performance through visual, velocity and acceleration analysis. Velocity is calculated as the change in Euclidean distance between consecutive points over time; Acceleration is the rate of change of velocity over time. Through this shape and subject specific complementary analysis to a spatial analysis of points drawn, a subject's fine temporal performance characteristics can be studied.
Figure 13C:
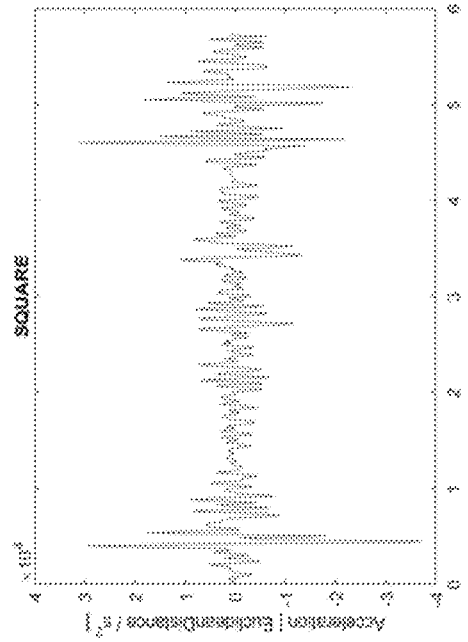
Figure 13A:
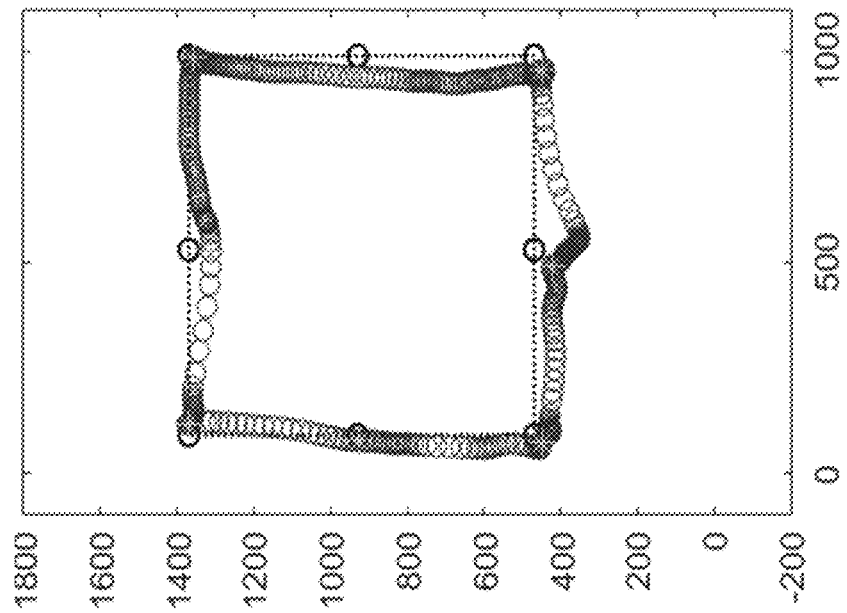

Finally, spatial and temporal characteristics of a subject drawing a square were determined and results are shown in FIG. 13.

Example 3: Results from the Prospective Pilot Study (FLOODLIGHT) to Evaluate the Feasibility of Conducting Remote Patient Monitoring with the Use of Digital Technology in Patients with Multiple Sclerosis A study population will be selected by using the following inclusion and exclusion criteria:

Key inclusion criteria:
Signed informed consent form
Able to comply with the study protocol, in the investigator's judgment
Age 18-55 years, inclusive
Have a definite diagnosis of MS, confirmed as per the revised McDonald 2010 criteria
EDSS score of 0.0 to 5.5, inclusive
Weight: 45-110 kg
For women of childbearing potential: agreement to use an acceptable birth control method during the study period
Key exclusion criteria:
Severely ill and unstable patients as per investigator's discretion
Change in dosing regimen or switch of disease modifying therapy (DMT) in the last 12 weeks prior to enrollment
Pregnant or lactating, or intending to become pregnant during the study It is a primary objective of this study to show adherence to smartphone and smartwatch-based assessments quantified as compliance level (%) and to obtain feedback from patients and healthy controls on the smartphone and smartwatch schedule of assessments and the impact on their daily activities using a satisfaction questionnaire. Furthermore, additional objectives are addressed, in particular, the association between assessments conducted using the Floodlight Test and conventional MS clinical outcomes was determined. It was established if Floodlight measures can be used as a marker for disease activity/progression and are associated with changes in MRI and clinical outcomes over time and it was determined if the Floodlight Test Battery can differentiate between patients with and without MS, and between phenotypes in patients with MS.

In addition to the active tests and passive monitoring, the following assessments will be performed at each scheduled clinic visit:

Oral Version of SDMT
Fatigue Scale for Motor and Cognitive Functions (FSMC)
Timed 25-Foot Walk Test (T25-FW)
Berg Balance Scale (BBS)
9-Hole Peg Test (SHPT)
Patient Health Questionnaire (PHQ-9)
Patients with MS only:
Brain MRI (MSmetrix)
Expanded Disability Status Scale (EDSS)
Patient Determined Disease Steps (PDDS)
Pen and paper version of MSIS-29

While performing in-clinic tests, patients and healthy controls will be asked to carry/wear a smartphone and smartwatch to collect sensor data along with in-clinic measures.

Figures 14A, 14B:
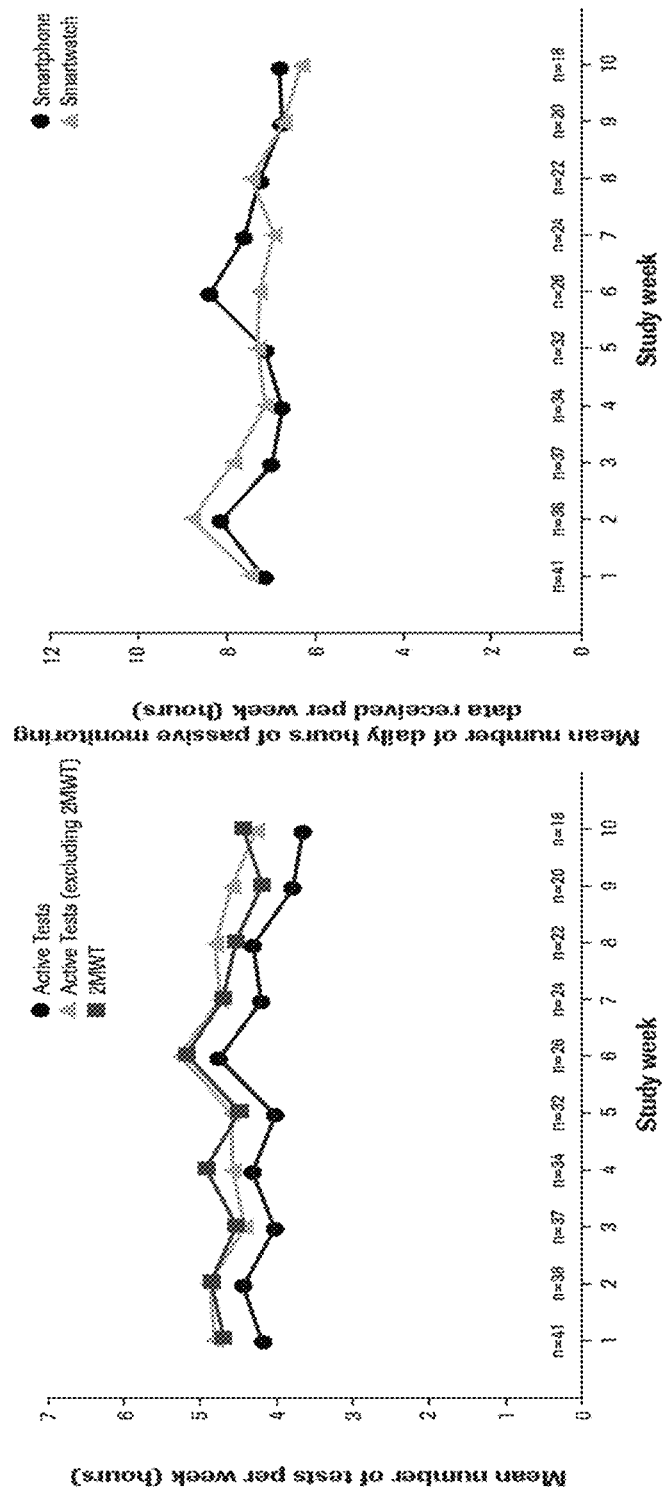
FIGS. 14A and 14B compare patient adherence to active tests and passive monitoring. Adherence count is based on adherent days per study week, defined as the week starting from the first data point received by the respective subject. Amount of passive monitoring collected is based on the duration of accelerometer recordings with correction for inactivity for smartphones and smartwatches individually. 2MWT, Two-Minute Walking Test.
Figure 15:
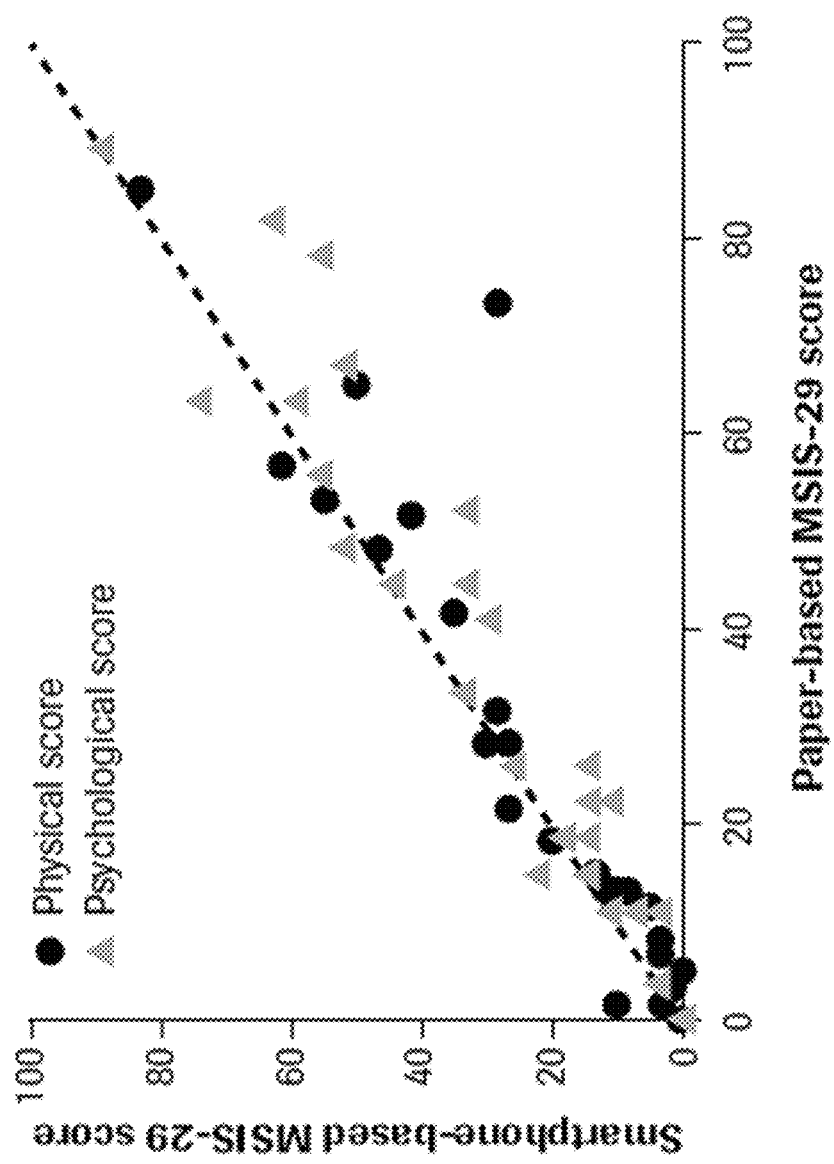
FIG. 15 shows an association between PROs conducted on the smartphone and in the clinic. Total scores of paper-based MSIS-29 and smartphone-based MSIS-29 are compared at baseline (screening visit). The identity line is depicted as a dashed line. MSIS-29, Multiple Sclerosis Impact Scale.
Figure 16:
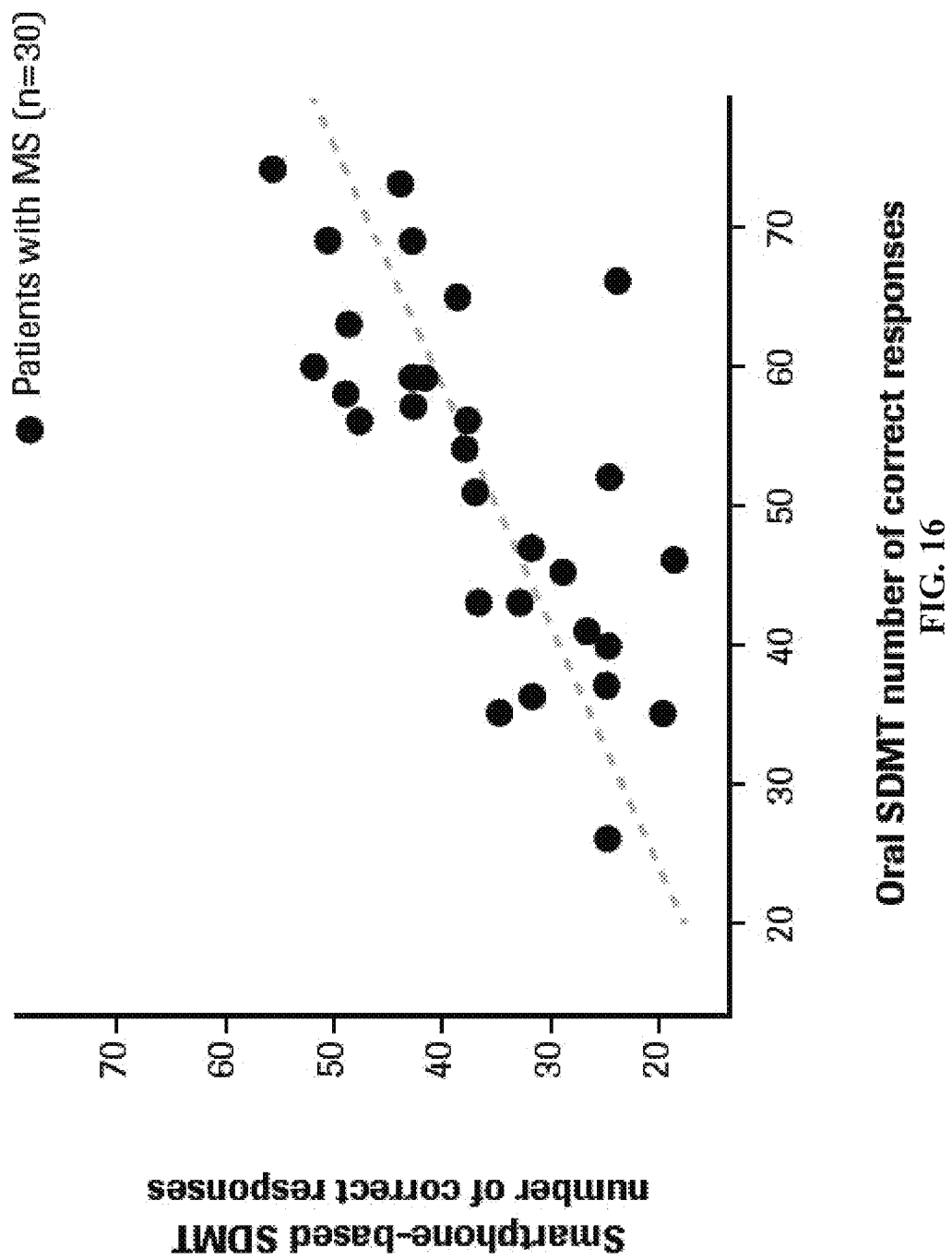
FIG. 16 shows a cross-sectional baseline correlation of oral SDMT vs. smartphone-based SDMT. At baseline, the number of correct responses from the smartphone-based SDMT correlated with correct responses from the oral SDMT (Spearman's correlation coefficient=0.72, p<0.001). The patient-level performances on oral SDMT were overall better than on the smartphone-based SDMT.
Figure 17A:
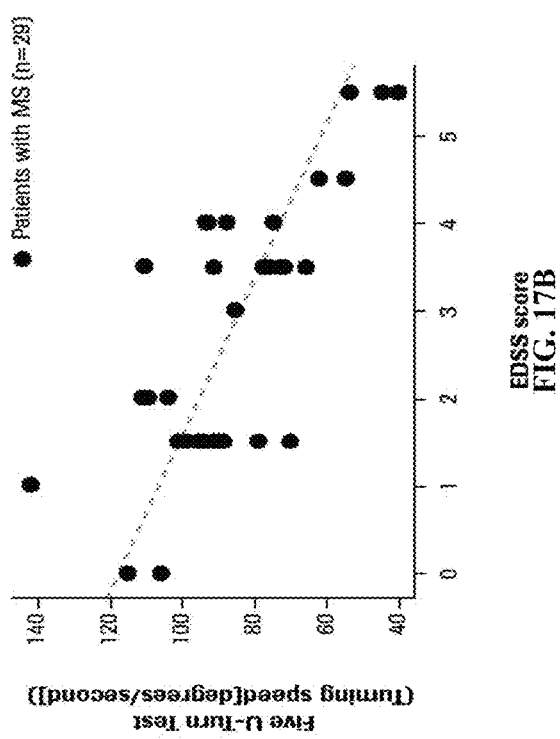
FIGS. 17A and 17B show that turning speed while walking correlates with (FIG. 17A) T25FW and (FIG. 17B) EDSS.
Figure 17B:
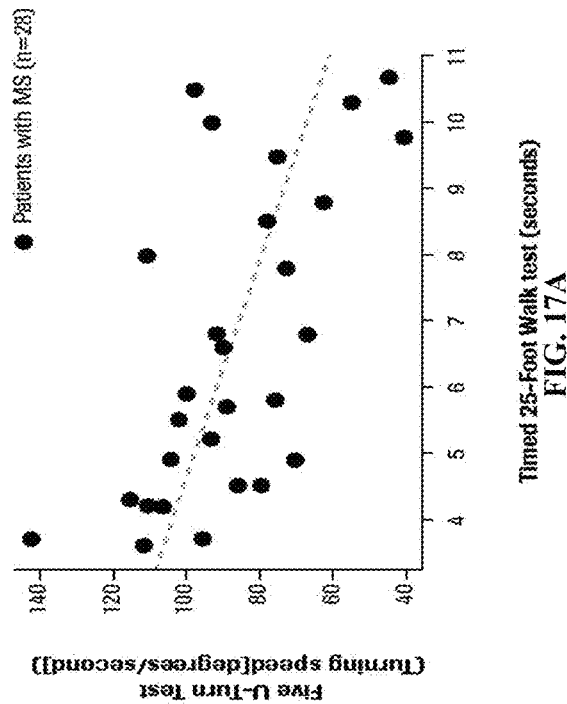

Patient adherence to active and passive testing is shown in FIG. 14. Furthermore, the association between PROs performed in the hospital and on a mobile device (smart phone) are shown in FIG. 15. A baseline correlation was found between oral SDMT and mobile device implemented eSDMT was found; see FIG. 16. The turning speed while walking correlates with T25FW and EDSS; see FIG. 17.

In summary, these results show that patients are highly engaged with the smartphone- and smartwatch-based assessments. Moreover, there is a correlation between tests and in-clinic clinical outcome measures recorded at baseline which suggests that the smartphone-based Floodlight Test Battery shall become a powerful tool to continuously monitor MS in a real-world scenario. Further, the smartphone-based measurement of turning speed while walking and performing U-turns appeared to correlate with T25FW and EDSS.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

CITED LITERATURE

Aktas 2005, Neuron 46, 421-432, Zamvil 2003, Neuron 38:685-688
Crawford A, et al. J Immunol 2006; 176(6):3498-506
Bar-Or A, et al. Ann Neurol 2010; 67(4):452-61
Lisak R P, et al. J Neuroimmunol 2012; 246(1-2):85-95
Weber M S, et al. Biochim Biophys Acta 2011; 1812(2): 239-45
Serafini B, et al. Brain Pathol 2004; 14(2):164-74
Magliozzi R, et al. Ann Neurol 2010; 68(4):477-93
Bove 2015, Neurol Neuroimmunol Neuroinflamm 2 (6): e162
Link 2006, J Neuroimmunol. 180 (1-2): 17-28
Tsang 2011, Australian family physician 40 (12): 948-55
Compston 2008, Lancet 372(9648): 1502-17
Johnston 2012, Drugs 72 (9): 1195-211
Polman 2011, Ann Neurol 69:292-302
Lublin 2014, Neurology 83: 278-286
Rai 2012, Proceedings of the 18th annual international conference on Mobile computing and networking. ACM
Alsheikh 2015, arXiv preprint arXiv:1511.04664
Ordóñez 2016, Sensors, 16(1), 115
Mancini 2012, J Neuroeng Rehabil. 22: 9:59
Hobart 2001, Brain 124: 962-73
Hutas 2008, Current opinion in investigational drugs 9 (11):1206-15
Köhler 1975, Nature 256: 495-497

What is claimed is:

1. A method of identifying progressing multiple sclerosis (MS) in a subject, the method comprising:
   a) using a mobile device having one or more sensors to obtain a dataset of activity measurements, wherein at least some of the activity measurements are obtained using a touch sensor configured to detect one or more activity measurements selected from the group consisting of double touch asynchrony, pinching target precision, pinching finger movement asymmetry, pinching finger velocity and pinching finger asynchrony;
   b) determining at least one performance parameter from the dataset of activity measurements obtained using the touch sensor;
   c) comparing the determined at least one performance parameter to a reference; and
   d) based upon the comparison of step c), identifying a subject with progressing MS.

2. The method of claim 1, wherein the touch sensor is configured to detect double touch asynchrony.

3. The method of claim 2, wherein the double touch asynchrony is detected during the Squeeze a Shape Test.

4. The method of claim 1, wherein said progressing multiple sclerosis is relapsing-remitting MS with clinical disease activity, is relapsing-remitting MS with disability progression, is secondary progressive MS, is secondary progressive MS with disability progression, is primary progressive MS, or is primary progressive MS with disability progression.

5. The method of claim 1, wherein the at least one performance parameter is a parameter indicative for the subject's motoric or fine motoric capabilities and function, walking, color vision, attention, dexterity or cognitive capabilities, quality of life, fatigue, mental state, mood, vision or cognition.

6. The method of claim 1, wherein the said dataset of activity measurements comprises data from the 2-Minute Walking Test (2MWT), 5 U-Turn Test (5UTT), Static balance test (SBT), eSDMT, CAG test, Draw a Shape test, and Squeeze a Shape test.

7. The method of claim 1, wherein said mobile device comprises a smartphone, smartwatch, wearable sensor, portable multimedia device or tablet computer.

8. The method of claim 1, wherein said reference is at least one performance parameter derived from a dataset of activity measurements obtained from the said subject at a time point prior to the time point when the dataset of activity measurements referred to in step a) has been obtained from the subject.

9. The method of claim 8, wherein a worsening between the determined at least one performance parameter and the reference is indicative for a subject with progressing MS.

10. The method of claim 1, wherein said reference is at least one performance parameter derived from a dataset of activity measurements obtained from a subject or group of subjects known to suffer from progressing MS.

11. The method of claim 10, wherein a determined at least one performance parameter being essentially identical compared to the reference is indicative for a subject with progressing MS.

12. The method of claim 1, wherein said reference is at least one performance parameter derived from a dataset of activity measurements obtained from a subject or group of subjects known not to suffer from progressing MS.

13. The method of claim 12, wherein a determined at least one performance parameter being worsened compared to the reference is indicative for a subject with progressing MS.

14. The method of claim 1 for use in recommending an anti-CD20 antibody therapy against MS, comprising the further step of recommending the anti-CD20 antibody therapy when progressing MS is identified.

15. The method of claim 14, further comprising administering the anti-CD20 antibody therapy to the subject.

16. The method of claim 14, wherein said anti-CD20 antibody is Ocrelizumab.

17. The method of claim 1 for use in determining efficacy of a therapy against progressing MS, comprising the further step of determining a therapy response if improvement of progressing MS occurs in the subject upon therapy or determining a failure of response if worsening of progressing MS occurs in the subject upon therapy or if the progressing MS remains unchanged.

18. The method of claim 1 for use in monitoring progressing MS in a subject, comprising determining whether progressing MS improves, worsens or remains unchanged in a subject by carrying out steps a)-c) at least two times during a predefined monitoring period.

19. A mobile device comprising a processor, at least one sensor, a database and software which is tangibly embedded in said device and, when running on said device, carries out the method of claim 1.

20. A system comprising a mobile device comprising at least one sensor and a remote device comprising a processor and a database as well as software which is tangibly embedded to said device and, when running on said device, carries out the method of claim 1, wherein said mobile device and said remote device are operatively linked to each other.

* * * * *